United States Patent
Lechmann et al.

(10) Patent No.: US 10,449,058 B2
(45) Date of Patent: Oct. 22, 2019

(54) EXPANDABLE INTERVERTEBRAL IMPLANT AND ASSOCIATED METHOD OF MANUFACTURING THE SAME

(71) Applicant: DePuy Synthes Products, Inc., Raynham, MA (US)

(72) Inventors: Beat Lechmann, Grenchen (CH); Dominique Burkard, Gretzenbach (CH); Johann Fierlbeck, Salzburg (AT); Alfred Niederberger, Grenchen (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/831,870

(22) Filed: Dec. 5, 2017

(65) Prior Publication Data
US 2018/0092755 A1    Apr. 5, 2018

Related U.S. Application Data

(63) Continuation of application No. 15/443,916, filed on Feb. 27, 2017, which is a continuation of application
(Continued)

(51) Int. Cl.
*A61F 2/44* (2006.01)
*A61F 2/30* (2006.01)
(Continued)

(52) U.S. Cl.
CPC .......... *A61F 2/4455* (2013.01); *A61F 2/3094* (2013.01); *A61F 2/30771* (2013.01);
(Continued)

(58) Field of Classification Search
CPC .......... A61F 2/44; A61F 2/4455; A61F 2/442; A61F 2/3094
See application file for complete search history.

(56) References Cited

U.S. PATENT DOCUMENTS

| | | |
|---|---|---|
| 1,802,560 A | 4/1931 | Kerwin |
| 1,924,695 A | 8/1933 | Olson |

(Continued)

FOREIGN PATENT DOCUMENTS

| | | |
|---|---|---|
| AU | 2005314079 B2 | 7/2012 |
| CN | 1177918 A | 4/1998 |

(Continued)

OTHER PUBLICATIONS

Zucherman, "A Multicenter, Prospective, Randomized Trial Evaluating the X STOP Interspinous Process Decompression System for the Treatment of Neurogenic Intermittent Claudication", SPINE, vol. 30, No. 12, pp. 1351-1358, 2005.

(Continued)

*Primary Examiner* — Christopher J Beccia
(74) *Attorney, Agent, or Firm* — BakerHostetler

(57) ABSTRACT

An expandable intervertebral implant (10) includes superior (20) and inferior (30) bone contacting members and at least one vertical wire netting (50) interconnecting the superior and inferior bone contacting members. The superior and inferior bone contacting members include at least two bone contacting components interconnected via one or more lateral wire nettings such that the implant is vertically and laterally expandable in situ from a first insertion configuration to a second expanded configuration. The vertical and lateral wire netting are preferably constructed of a plurality of individual link members. The present invention also preferably relates to an associated method of manufacturing the intervertebral implant such that the intervertebral implant can be manufactured as an integral component or part.

21 Claims, 19 Drawing Sheets

Related U.S. Application Data

No. 15/221,169, filed on Jul. 27, 2016, now Pat. No. 9,597,197, which is a continuation of application No. 14/724,082, filed on May 28, 2015, now Pat. No. 9,433,510, which is a continuation of application No. 14/032,231, filed on Sep. 20, 2013, now Pat. No. 9,295,562, which is a continuation of application No. 12/812,146, filed as application No. PCT/US2009/031567 on Jan. 21, 2009, now Pat. No. 8,551,173.

(60) Provisional application No. 61/021,778, filed on Jan. 17, 2008.

(51) Int. Cl.
  *B33Y 80/00* (2015.01)
  B33Y 10/00 (2015.01)
  B22F 3/105 (2006.01)

(52) U.S. Cl.
  CPC .............. *A61F 2/44* (2013.01); *A61F 2/442* (2013.01); *A61F 2/4425* (2013.01); *B33Y 80/00* (2014.12); *A61F 2002/3055* (2013.01); *A61F 2002/30462* (2013.01); *A61F 2002/30518* (2013.01); *A61F 2002/30556* (2013.01); *A61F 2002/30579* (2013.01); *A61F 2002/30785* (2013.01); *A61F 2002/30843* (2013.01); *A61F 2002/30904* (2013.01); *A61F 2002/4475* (2013.01); *A61F 2002/4495* (2013.01); *A61F 2220/0016* (2013.01); *A61F 2250/0009* (2013.01); *B22F 3/1055* (2013.01); *B33Y 10/00* (2014.12)

(56) References Cited

U.S. PATENT DOCUMENTS

| | | |
|---|---|---|
| 2,077,804 A | 4/1937 | Morrison |
| 2,121,193 A | 6/1938 | Hanicke |
| 2,173,655 A | 9/1939 | Neracher et al. |
| 2,243,717 A | 5/1941 | Moreira |
| 2,381,050 A | 8/1945 | Hardinge |
| 2,388,056 A | 10/1945 | Hendricks |
| 2,485,531 A | 10/1949 | William et al. |
| 2,489,870 A | 11/1949 | Dzus |
| 2,570,465 A | 10/1951 | Lundholm |
| 2,677,369 A | 5/1954 | Knowles |
| 2,746,385 A | 5/1956 | Muller |
| 3,115,804 A | 12/1963 | Johnson |
| 3,312,139 A | 4/1967 | Di Cristina |
| 3,486,505 A | 12/1969 | Morrison |
| 3,489,143 A | 1/1970 | Halloran |
| 3,698,391 A | 10/1972 | Mahony |
| 3,760,802 A | 9/1973 | Fischer et al. |
| 3,805,775 A | 4/1974 | Fischer et al. |
| 3,811,449 A | 5/1974 | Gravlee et al. |
| 3,842,825 A | 10/1974 | Wagner |
| 3,848,601 A | 11/1974 | Ma et al. |
| 3,867,728 A | 2/1975 | Stubstad et al. |
| 3,986,504 A | 10/1976 | Avila |
| 4,013,071 A | 3/1977 | Rosenberg |
| 4,052,988 A | 10/1977 | Doddi et al. |
| 4,091,806 A | 5/1978 | Aginsky |
| 4,175,555 A | 11/1979 | Herbert |
| 4,236,512 A | 12/1980 | Aginsky |
| 4,262,665 A | 4/1981 | Roalstad et al. |
| 4,275,717 A | 6/1981 | Bolesky |
| 4,312,353 A | 1/1982 | Shahbabian |
| 4,341,206 A | 7/1982 | Perrett et al. |
| 4,349,921 A | 9/1982 | Kuntz |
| 4,350,151 A | 9/1982 | Scott |
| 4,369,790 A | 1/1983 | McCarthy |
| 4,401,112 A | 8/1983 | Rezaian |
| 4,401,433 A | 8/1983 | Luther |
| 4,409,974 A | 10/1983 | Freedland |
| 4,449,532 A | 5/1984 | Storz |
| 4,451,256 A | 5/1984 | Weikl et al. |
| 4,456,005 A | 6/1984 | Lichty |
| 4,463,753 A | 8/1984 | Gustilo |
| 4,488,543 A | 12/1984 | Tornier |
| 4,494,535 A | 1/1985 | Haig |
| 4,532,660 A | 8/1985 | Field |
| 4,537,185 A | 8/1985 | Stednitz |
| 4,545,374 A | 10/1985 | Jacobson |
| 4,573,448 A | 3/1986 | Kambin |
| 4,601,710 A | 7/1986 | Moll |
| 4,625,725 A | 12/1986 | Davison et al. |
| 4,629,450 A | 12/1986 | Suzuki et al. |
| 4,632,101 A | 12/1986 | Freedland |
| 4,640,271 A | 2/1987 | Lower |
| 4,641,640 A | 2/1987 | Griggs |
| 4,653,489 A | 3/1987 | Tronzo |
| 4,667,663 A | 5/1987 | Miyata |
| 4,686,984 A | 8/1987 | Bonnet |
| 4,688,561 A | 8/1987 | Reese |
| 4,721,103 A | 1/1988 | Freedland |
| 4,723,544 A | 2/1988 | Moore et al. |
| 4,743,257 A | 5/1988 | Toermaelae et al. |
| 4,759,766 A | 7/1988 | Buettner-Janz et al. |
| 4,760,843 A | 8/1988 | Fischer et al. |
| 4,790,304 A | 12/1988 | Rosenberg |
| 4,790,817 A | 12/1988 | Luther |
| 4,796,612 A | 1/1989 | Reese |
| 4,802,479 A | 2/1989 | Haber et al. |
| 4,815,909 A | 3/1989 | Simons |
| 4,827,917 A | 5/1989 | Brumfield |
| 4,858,601 A | 8/1989 | Glisson |
| 4,862,891 A | 9/1989 | Smith |
| 4,863,476 A | 9/1989 | Shepperd |
| 4,873,976 A | 10/1989 | Schreiber |
| 4,898,186 A | 2/1990 | Ikada et al. |
| 4,903,692 A | 2/1990 | Reese |
| 4,917,554 A | 4/1990 | Bronn |
| 4,940,467 A | 7/1990 | Tronzo |
| 4,959,064 A | 9/1990 | Engelhardt |
| 4,963,144 A | 10/1990 | Huene |
| 4,966,587 A | 10/1990 | Baumgart |
| 4,968,317 A | 11/1990 | Toermaelae et al. |
| 4,978,334 A | 12/1990 | Toye et al. |
| 4,978,349 A | 12/1990 | Frigg |
| 4,981,482 A | 1/1991 | Ichikawa |
| 4,988,351 A | 1/1991 | Paulos et al. |
| 4,994,027 A | 2/1991 | Farrell |
| 5,002,557 A | 3/1991 | Hasson |
| 5,011,484 A | 4/1991 | Breard |
| 5,013,315 A | 5/1991 | Barrows |
| 5,013,316 A | 5/1991 | Goble et al. |
| 5,059,193 A | 10/1991 | Kuslich |
| 5,062,849 A | 11/1991 | Schelhas |
| 5,080,662 A | 1/1992 | Paul |
| 5,084,043 A | 1/1992 | Hertzmann et al. |
| 5,092,891 A | 3/1992 | Kummer et al. |
| 5,098,241 A | 3/1992 | Aldridge et al. |
| 5,098,433 A | 3/1992 | Freedland |
| 5,098,435 A | 3/1992 | Stednitz et al. |
| 5,114,407 A | 5/1992 | Burbank |
| 5,116,336 A | 5/1992 | Frigg |
| 5,120,171 A | 6/1992 | Lasner |
| 5,122,133 A | 6/1992 | Evans |
| 5,122,141 A | 6/1992 | Simpson et al. |
| 5,123,926 A | 6/1992 | Pisharodi |
| 5,139,486 A | 8/1992 | Moss |
| 5,158,543 A | 10/1992 | Lazarus |
| 5,167,663 A | 12/1992 | Brumfield |
| 5,167,664 A | 12/1992 | Hodorek |
| 5,169,400 A | 12/1992 | Muehling et al. |
| 5,171,278 A | 12/1992 | Pisharodi |
| 5,171,279 A | 12/1992 | Mathews |
| 5,171,280 A | 12/1992 | Baumgartner |
| 5,176,651 A | 1/1993 | Allgood et al. |
| 5,176,697 A | 1/1993 | Hasson et al. |
| 5,178,501 A | 1/1993 | Carstairs |
| 5,183,464 A | 2/1993 | Dubrul et al. |

(56) References Cited

U.S. PATENT DOCUMENTS

| | | |
|---|---|---|
| 5,188,118 A | 2/1993 | Terwilliger |
| 5,195,506 A | 3/1993 | Hulfish |
| 5,201,742 A | 4/1993 | Hasson |
| 5,217,462 A | 6/1993 | Asnis et al. |
| 5,217,486 A | 6/1993 | Rice et al. |
| 5,224,952 A | 7/1993 | Deniega et al. |
| 5,234,431 A | 8/1993 | Keller |
| 5,241,972 A | 9/1993 | Bonati |
| 5,242,410 A | 9/1993 | Melker |
| 5,242,447 A | 9/1993 | Borzone |
| 5,246,441 A | 9/1993 | Ross et al. |
| 5,250,049 A | 10/1993 | Michael |
| 5,269,797 A | 12/1993 | Bonati et al. |
| 5,280,782 A | 1/1994 | Wilk |
| 5,286,001 A | 2/1994 | Rafeld |
| 5,290,243 A | 3/1994 | Chodorow et al. |
| 5,290,312 A | 3/1994 | Kojimoto et al. |
| 5,300,074 A | 4/1994 | Frigg |
| 5,304,142 A | 4/1994 | Liebl et al. |
| 5,308,327 A | 5/1994 | Heaven et al. |
| 5,308,352 A | 5/1994 | Koutrouvelis |
| 5,312,410 A | 5/1994 | Miller et al. |
| 5,312,417 A | 5/1994 | Wilk |
| 5,314,477 A | 5/1994 | Marnay |
| 5,324,261 A | 6/1994 | Amundson et al. |
| 5,334,184 A | 8/1994 | Bimman |
| 5,334,204 A | 8/1994 | Clewett et al. |
| 5,342,365 A | 8/1994 | Waldman |
| 5,342,382 A | 8/1994 | Brinkerhoff et al. |
| 5,344,252 A | 9/1994 | Kakimoto |
| 5,364,398 A | 11/1994 | Chapman et al. |
| 5,370,646 A | 12/1994 | Reese et al. |
| 5,370,647 A | 12/1994 | Graber et al. |
| 5,370,661 A | 12/1994 | Branch |
| 5,370,697 A * | 12/1994 | Baumgartner ......... A61F 2/442 623/17.15 |
| 5,382,248 A | 1/1995 | Jacobson et al. |
| 5,387,213 A | 2/1995 | Breard et al. |
| 5,387,215 A | 2/1995 | Fisher |
| 5,390,683 A | 2/1995 | Pisharodi |
| 5,395,317 A | 3/1995 | Kambin |
| 5,395,371 A | 3/1995 | Miller et al. |
| 5,401,269 A | 3/1995 | Buettner-Janz et al. |
| 5,407,430 A | 4/1995 | Peters |
| 5,415,661 A | 5/1995 | Holmes |
| 5,424,773 A | 6/1995 | Saito |
| 5,425,773 A | 6/1995 | Boyd et al. |
| 5,443,514 A | 8/1995 | Steffee |
| 5,449,359 A | 9/1995 | Groiso |
| 5,449,361 A | 9/1995 | Preissman |
| 5,452,748 A | 9/1995 | Simmons et al. |
| 5,454,790 A | 10/1995 | Dubrul |
| 5,464,427 A | 11/1995 | Curtis et al. |
| 5,470,333 A | 11/1995 | Ray |
| 5,472,426 A | 12/1995 | Bonati et al. |
| 5,474,539 A | 12/1995 | Costa et al. |
| 5,486,190 A | 1/1996 | Green |
| 5,496,318 A | 3/1996 | Howland et al. |
| 5,498,265 A | 3/1996 | Asnis et al. |
| 5,501,695 A | 3/1996 | Anspach et al. |
| 5,505,710 A | 4/1996 | Dorsey, III |
| 5,507,816 A | 4/1996 | Bullivant |
| 5,512,037 A | 4/1996 | Russell et al. |
| 5,514,180 A | 5/1996 | Heggeness et al. |
| 5,520,690 A | 5/1996 | Errico et al. |
| 5,520,896 A | 5/1996 | De et al. |
| 5,522,899 A | 6/1996 | Michelson |
| 5,527,312 A | 6/1996 | Ray |
| 5,534,029 A | 7/1996 | Shima |
| 5,536,127 A | 7/1996 | Pennig |
| 5,540,688 A | 7/1996 | Navas |
| 5,540,693 A | 7/1996 | Fisher |
| 5,545,164 A | 8/1996 | Howland |
| 5,549,610 A | 8/1996 | Russell et al. |
| 5,554,191 A | 9/1996 | Lahille et al. |
| 5,556,431 A | 9/1996 | Buettner-Janz |
| 5,558,674 A | 9/1996 | Heggeness et al. |
| D374,287 S | 10/1996 | Goble et al. |
| 5,562,738 A | 10/1996 | Boyd et al. |
| 5,564,926 A | 10/1996 | Braanemark |
| 5,569,248 A | 10/1996 | Mathews |
| 5,569,251 A | 10/1996 | Baker et al. |
| 5,569,290 A | 10/1996 | McAfee |
| 5,569,548 A | 10/1996 | Koike et al. |
| 5,591,168 A | 1/1997 | Judet et al. |
| 5,609,634 A | 3/1997 | Voydeville |
| 5,609,635 A | 3/1997 | Michelson |
| 5,613,950 A | 3/1997 | Yoon |
| 5,618,142 A | 4/1997 | Sonden et al. |
| 5,618,314 A | 4/1997 | Harwin et al. |
| 5,624,447 A | 4/1997 | Myers |
| 5,626,613 A | 5/1997 | Schmieding |
| 5,628,751 A | 5/1997 | Sander et al. |
| 5,628,752 A | 5/1997 | Asnis et al. |
| 5,639,276 A | 6/1997 | Weinstock et al. |
| 5,643,320 A | 7/1997 | Lower et al. |
| 5,645,589 A | 7/1997 | Li |
| 5,645,599 A | 7/1997 | Samani |
| 5,647,857 A | 7/1997 | Anderson et al. |
| 5,649,931 A | 7/1997 | Bryant et al. |
| 5,653,763 A | 8/1997 | Errico et al. |
| 5,658,335 A | 8/1997 | Allen |
| 5,662,658 A | 9/1997 | Wenstrom, Jr. |
| 5,662,683 A | 9/1997 | Kay |
| 5,665,095 A | 9/1997 | Jacobson et al. |
| 5,665,122 A | 9/1997 | Kambin |
| 5,667,508 A | 9/1997 | Errico et al. |
| 5,669,915 A | 9/1997 | Caspar et al. |
| 5,676,701 A | 10/1997 | Yuan et al. |
| 5,683,465 A | 11/1997 | Shinn et al. |
| 5,693,100 A | 12/1997 | Pisharodi |
| 5,697,977 A | 12/1997 | Pisharodi |
| 5,702,391 A | 12/1997 | Lin |
| 5,707,359 A | 1/1998 | Bufalini |
| 5,713,870 A | 2/1998 | Yoon |
| 5,713,903 A | 2/1998 | Sander et al. |
| 5,716,415 A | 2/1998 | Steffee |
| 5,716,416 A | 2/1998 | Lin |
| 5,720,753 A | 2/1998 | Sander et al. |
| 5,725,541 A | 3/1998 | Anspach et al. |
| 5,725,588 A | 3/1998 | Errico et al. |
| 5,728,097 A | 3/1998 | Mathews |
| 5,728,116 A | 3/1998 | Rosenman |
| 5,735,853 A | 4/1998 | Olerud |
| 5,741,282 A | 4/1998 | Anspach et al. |
| 5,743,881 A | 4/1998 | Demco |
| 5,743,912 A | 4/1998 | Lahille et al. |
| 5,743,914 A | 4/1998 | Skiba |
| 5,749,889 A | 5/1998 | Bacich et al. |
| 5,752,969 S | 5/1998 | Cunci et al. |
| 5,762,500 A | 6/1998 | Lazarof |
| 5,762,629 A | 6/1998 | Kambin |
| 5,772,661 A | 6/1998 | Michelson |
| 5,772,662 A | 6/1998 | Chapman et al. |
| 5,772,678 A | 6/1998 | Thomason et al. |
| 5,776,156 A | 7/1998 | Shikhman |
| 5,782,800 A | 7/1998 | Yoon |
| 5,782,832 A | 7/1998 | Larsen et al. |
| 5,782,865 A | 7/1998 | Grotz |
| 5,792,044 A | 8/1998 | Foley et al. |
| 5,810,721 A | 9/1998 | Mueller et al. |
| 5,810,821 A | 9/1998 | Vandewalle |
| 5,810,866 A | 9/1998 | Yoon |
| 5,814,084 A | 9/1998 | Grivas et al. |
| 5,836,948 A | 11/1998 | Zucherman et al. |
| 5,846,259 A | 12/1998 | Berthiaume |
| 5,849,004 A | 12/1998 | Bramlet |
| 5,851,216 A | 12/1998 | Allen |
| 5,860,973 A | 1/1999 | Michelson |
| 5,860,977 A | 1/1999 | Zucherman et al. |
| 5,865,848 A | 2/1999 | Baker |
| 5,871,485 A | 2/1999 | Rao et al. |
| 5,873,854 A | 2/1999 | Wolvek |
| 5,876,404 A | 3/1999 | Zucherman et al. |

(56) References Cited

U.S. PATENT DOCUMENTS

| | | |
|---|---|---|
| 5,888,223 A | 3/1999 | Bray, Jr. |
| 5,888,224 A | 3/1999 | Beckers et al. |
| 5,888,226 A | 3/1999 | Rogozinski |
| 5,888,228 A | 3/1999 | Knothe et al. |
| 5,893,850 A | 4/1999 | Cachia |
| 5,893,889 A | 4/1999 | Harrington |
| 5,893,890 A | 4/1999 | Pisharodi |
| 5,895,428 A | 4/1999 | Berry |
| 5,902,231 A | 5/1999 | Foley et al. |
| 5,904,696 A | 5/1999 | Rosenman |
| 5,908,422 A | 6/1999 | Bresina |
| 5,928,235 A | 7/1999 | Friedl |
| 5,928,244 A | 7/1999 | Tovey et al. |
| 5,928,422 A | 7/1999 | Uchiyama et al. |
| 5,931,870 A | 8/1999 | Cuckler et al. |
| 5,935,129 A | 8/1999 | McDevitt et al. |
| 5,947,999 A | 9/1999 | Groiso |
| 5,948,000 A | 9/1999 | Larsen et al. |
| 5,954,722 A | 9/1999 | Bono |
| 5,954,747 A | 9/1999 | Clark |
| 5,957,902 A | 9/1999 | Teves |
| 5,957,924 A | 9/1999 | Toermaelae et al. |
| 5,964,730 A | 10/1999 | Williams et al. |
| 5,964,761 A | 10/1999 | Kambin |
| 5,967,783 A | 10/1999 | Ura |
| 5,967,970 A | 10/1999 | Cowan et al. |
| 5,968,044 A | 10/1999 | Nicholson et al. |
| 5,968,098 A | 10/1999 | Winslow |
| 5,976,139 A | 11/1999 | Bramlet |
| 5,976,146 A | 11/1999 | Ogawa et al. |
| 5,976,186 A | 11/1999 | Bao et al. |
| 5,980,522 A | 11/1999 | Koros et al. |
| 5,984,927 A | 11/1999 | Wenstrom et al. |
| 5,984,966 A | 11/1999 | Kiema et al. |
| 5,989,255 A | 11/1999 | Pepper et al. |
| 5,989,291 A | 11/1999 | Ralph et al. |
| 5,993,459 A | 11/1999 | Larsen et al. |
| 5,997,510 A | 12/1999 | Schwemberger |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke |
| 6,007,519 A | 12/1999 | Rosselli |
| 6,007,566 A | 12/1999 | Wenstrom, Jr. |
| 6,007,580 A | 12/1999 | Lehto et al. |
| 6,010,513 A | 1/2000 | Toermaelae et al. |
| 6,015,410 A | 1/2000 | Toermaelae et al. |
| 6,019,762 A | 2/2000 | Cole |
| 6,022,352 A | 2/2000 | Vandewalle |
| 6,030,162 A | 2/2000 | Huebner |
| 6,030,364 A | 2/2000 | Durgin et al. |
| 6,033,406 A | 3/2000 | Mathews |
| 6,036,701 A | 3/2000 | Rosenman |
| 6,039,761 A | 3/2000 | Li et al. |
| 6,039,763 A | 3/2000 | Shelokov |
| 6,045,579 A | 4/2000 | Hochschuler et al. |
| 6,048,309 A | 4/2000 | Flom et al. |
| 6,048,342 A | 4/2000 | Zucherman et al. |
| 6,053,935 A | 4/2000 | Brenneman et al. |
| 6,066,142 A | 5/2000 | Serbousek et al. |
| 6,068,630 A | 5/2000 | Zucherman et al. |
| 6,068,648 A | 5/2000 | Cole et al. |
| 6,074,390 A | 6/2000 | Zucherman et al. |
| 6,080,193 A | 6/2000 | Hochschuler et al. |
| 6,083,244 A | 7/2000 | Lubbers et al. |
| 6,090,112 A | 7/2000 | Zucherman et al. |
| 6,099,531 A | 8/2000 | Bonutti |
| 6,102,914 A | 8/2000 | Bulstra et al. |
| 6,102,950 A | 8/2000 | Vaccaro |
| 6,106,557 A | 8/2000 | Robioneck et al. |
| 6,113,637 A | 9/2000 | Gill et al. |
| 6,113,638 A | 9/2000 | Williams et al. |
| 6,117,174 A | 9/2000 | Nolan |
| 6,123,711 A | 9/2000 | Winters |
| 6,126,661 A | 10/2000 | Faccioli et al. |
| 6,126,663 A | 10/2000 | Hair |
| 6,127,597 A | 10/2000 | Beyar et al. |
| 6,129,762 A | 10/2000 | Li |
| 6,129,763 A | 10/2000 | Chauvin et al. |
| 6,146,384 A | 11/2000 | Lee et al. |
| 6,146,387 A | 11/2000 | Trott et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,179 A | 12/2000 | Simonson |
| 6,161,350 A | 12/2000 | Espinosa |
| 6,162,234 A | 12/2000 | Freedland et al. |
| 6,162,236 A | 12/2000 | Osada |
| 6,168,595 B1 | 1/2001 | Durham et al. |
| 6,168,597 B1 | 1/2001 | Biedermann et al. |
| 6,175,758 B1 | 1/2001 | Kambin |
| 6,176,882 B1 | 1/2001 | Biedermann et al. |
| 6,179,794 B1 | 1/2001 | Burras |
| 6,179,873 B1 | 1/2001 | Zientek |
| 6,183,471 B1 | 2/2001 | Zucherman et al. |
| 6,183,472 B1 | 2/2001 | Lutz |
| 6,183,474 B1 | 2/2001 | Bramlet et al. |
| 6,183,517 B1 | 2/2001 | Suddaby |
| 6,190,387 B1 | 2/2001 | Zucherman et al. |
| 6,193,757 B1 | 2/2001 | Foley et al. |
| 6,197,041 B1 | 3/2001 | Shichman et al. |
| 6,200,322 B1 | 3/2001 | Branch et al. |
| 6,206,826 B1 | 3/2001 | Mathews et al. |
| 6,206,922 B1 | 3/2001 | Zdeblick et al. |
| 6,213,957 B1 | 4/2001 | Milliman et al. |
| 6,217,509 B1 | 4/2001 | Foley et al. |
| 6,221,082 B1 | 4/2001 | Marino et al. |
| 6,228,058 B1 | 5/2001 | Dennis et al. |
| 6,231,606 B1 | 5/2001 | Graf et al. |
| 6,235,030 B1 | 5/2001 | Zucherman et al. |
| 6,238,397 B1 | 5/2001 | Zucherman et al. |
| 6,245,107 B1 | 6/2001 | Ferree |
| 6,248,108 B1 | 6/2001 | Toermaelae et al. |
| 6,251,111 B1 | 6/2001 | Barker et al. |
| 6,264,676 B1 | 7/2001 | Gellman et al. |
| 6,267,765 B1 | 7/2001 | Taylor et al. |
| 6,267,767 B1 | 7/2001 | Strobel et al. |
| 6,280,444 B1 | 8/2001 | Zucherman et al. |
| 6,287,313 B1 | 9/2001 | Sasso |
| 6,293,909 B1 | 9/2001 | Chu et al. |
| 6,293,952 B1 | 9/2001 | Brosens et al. |
| 6,296,647 B1 | 10/2001 | Robioneck et al. |
| 6,302,914 B1 | 10/2001 | Michelson |
| 6,306,136 B1 | 10/2001 | Baccelli |
| 6,319,254 B1 | 11/2001 | Giet et al. |
| 6,319,272 B1 | 11/2001 | Brenneman et al. |
| 6,332,882 B1 | 12/2001 | Zucherman et al. |
| 6,332,883 B1 | 12/2001 | Zucherman et al. |
| 6,332,895 B1 | 12/2001 | Suddaby |
| 6,346,092 B1 | 2/2002 | Leschinsky |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,361,557 B1 | 3/2002 | Gittings et al. |
| 6,364,897 B1 | 4/2002 | Bonutti |
| 6,368,350 B1 | 4/2002 | Erickson et al. |
| 6,368,351 B1 | 4/2002 | Glenn et al. |
| 6,371,971 B1 | 4/2002 | Tsugita et al. |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,379,363 B1 | 4/2002 | Herrington et al. |
| 6,387,130 B1 | 5/2002 | Stone et al. |
| 6,409,766 B1 | 6/2002 | Brett |
| 6,409,767 B1 | 6/2002 | Perice et al. |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,705 B1 | 7/2002 | Erickson |
| 6,419,706 B1 | 7/2002 | Graf |
| 6,423,061 B1 | 7/2002 | Bryant |

(56) References Cited

U.S. PATENT DOCUMENTS

| | | |
|---|---|---|
| 6,423,067 B1 | 7/2002 | Eisermann |
| 6,425,919 B1 | 7/2002 | Lambrecht |
| 6,428,541 B1 | 8/2002 | Boyd et al. |
| 6,428,556 B1 | 8/2002 | Chin |
| 6,436,140 B1 | 8/2002 | Liu et al. |
| 6,436,143 B1 | 8/2002 | Ross et al. |
| 6,440,154 B2 | 8/2002 | Gellman et al. |
| 6,440,169 B1 | 8/2002 | Elberg et al. |
| 6,443,989 B1 | 9/2002 | Jackson |
| 6,447,527 B1 | 9/2002 | Thompson et al. |
| 6,447,540 B1 | 9/2002 | Fontaine et al. |
| 6,450,989 B2 | 9/2002 | Dubrul et al. |
| 6,451,019 B1 | 9/2002 | Zucherman et al. |
| 6,451,020 B1 | 9/2002 | Zucherman et al. |
| 6,454,806 B1 | 9/2002 | Cohen et al. |
| 6,454,807 B1 | 9/2002 | Jackson |
| 6,458,134 B1 | 10/2002 | Songer et al. |
| 6,468,277 B1 | 10/2002 | Justin et al. |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,475,226 B1 | 11/2002 | Belef et al. |
| 6,478,029 B1 | 11/2002 | Boyd et al. |
| 6,478,796 B2 | 11/2002 | Zucherman et al. |
| 6,485,491 B1 | 11/2002 | Farris et al. |
| 6,485,518 B1 | 11/2002 | Cornwall et al. |
| 6,488,693 B2 | 12/2002 | Gannoe et al. |
| 6,488,710 B2 | 12/2002 | Besselink |
| 6,489,309 B1 | 12/2002 | Singh et al. |
| 6,491,714 B1 | 12/2002 | Bennett |
| 6,494,860 B2 | 12/2002 | Rocamora et al. |
| 6,494,893 B2 | 12/2002 | Dubrul et al. |
| 6,500,178 B2 | 12/2002 | Zucherman et al. |
| 6,506,192 B1 | 1/2003 | Gertzman et al. |
| 6,511,481 B2 | 1/2003 | Von et al. |
| 6,514,256 B2 | 2/2003 | Zucherman et al. |
| 6,517,543 B1 | 2/2003 | Berrevoets et al. |
| 6,517,580 B1 | 2/2003 | Ramadan et al. |
| 6,520,907 B1 | 2/2003 | Foley et al. |
| 6,527,774 B2 | 3/2003 | Lieberman |
| 6,527,803 B1 | 3/2003 | Crozet et al. |
| 6,527,804 B1 | 3/2003 | Gauchet et al. |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,551,319 B2 | 4/2003 | Lieberman |
| 6,551,322 B1 | 4/2003 | Lieberman |
| 6,554,831 B1 | 4/2003 | Rivard et al. |
| 6,554,852 B1 | 4/2003 | Oberlander |
| 6,558,389 B2 | 5/2003 | Clark et al. |
| 6,558,424 B2 | 5/2003 | Thalgott |
| 6,562,046 B2 | 5/2003 | Sasso |
| 6,562,049 B1 | 5/2003 | Norlander et al. |
| 6,562,074 B2 | 5/2003 | Gerbec et al. |
| 6,575,979 B1 | 6/2003 | Cragg |
| 6,576,016 B1 | 6/2003 | Hochshuler et al. |
| 6,579,293 B1 | 6/2003 | Chandran |
| 6,582,390 B1 | 6/2003 | Sanderson |
| 6,582,431 B1 | 6/2003 | Ray |
| 6,582,433 B2 | 6/2003 | Yun |
| 6,582,437 B2 | 6/2003 | Dorchak et al. |
| 6,582,441 B1 | 6/2003 | He et al. |
| 6,582,453 B1 | 6/2003 | Tran et al. |
| 6,582,468 B1 | 6/2003 | Gauchet |
| 6,585,730 B1 | 7/2003 | Foerster |
| 6,585,740 B2 | 7/2003 | Schlapfer et al. |
| 6,589,240 B2 | 7/2003 | Hinchliffe |
| 6,589,249 B2 | 7/2003 | Sater et al. |
| 6,592,553 B2 | 7/2003 | Zhang et al. |
| 6,595,998 B2 | 7/2003 | Johnson et al. |
| 6,596,008 B1 | 7/2003 | Kambin |
| 6,599,297 B1 | 7/2003 | Carlsson et al. |
| 6,607,530 B1 | 8/2003 | Carl et al. |
| 6,610,091 B1 | 8/2003 | Reiley |
| 6,610,094 B2 | 8/2003 | Husson |
| 6,613,050 B1 | 9/2003 | Wagner et al. |
| 6,616,678 B2 | 9/2003 | Nishtala et al. |
| 6,620,196 B1 | 9/2003 | Trieu |
| 6,626,944 B1 | 9/2003 | Taylor |
| 6,632,224 B2 | 10/2003 | Cachia et al. |
| 6,635,059 B2 | 10/2003 | Randall et al. |
| 6,635,362 B2 | 10/2003 | Zheng |
| 6,641,564 B1 | 11/2003 | Kraus |
| 6,641,614 B1 | 11/2003 | Wagner et al. |
| 6,645,248 B2 | 11/2003 | Casutt |
| 6,648,890 B2 | 11/2003 | Culbert et al. |
| 6,648,893 B2 | 11/2003 | Dudasik |
| 6,648,917 B2 | 11/2003 | Gerbec et al. |
| 6,652,527 B2 | 11/2003 | Zucherman et al. |
| 6,655,962 B1 | 12/2003 | Kennard |
| 6,666,891 B2 | 12/2003 | Boehm et al. |
| 6,669,698 B1 | 12/2003 | Tromanhauser et al. |
| 6,669,729 B2 | 12/2003 | Chin |
| 6,673,074 B2 | 1/2004 | Shluzas |
| 6,676,664 B1 | 1/2004 | Al-Assir |
| 6,676,665 B2 | 1/2004 | Foley et al. |
| 6,679,833 B2 | 1/2004 | Smith et al. |
| 6,682,535 B2 | 1/2004 | Hoogland |
| 6,685,706 B2 | 2/2004 | Padget et al. |
| 6,685,742 B1 | 2/2004 | Jackson |
| 6,689,152 B2 | 2/2004 | Balceta et al. |
| 6,692,499 B2 | 2/2004 | Toermaelae et al. |
| 6,695,842 B2 | 2/2004 | Zucherman et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,712,819 B2 | 3/2004 | Zucherman et al. |
| 6,716,247 B2 | 4/2004 | Michelson |
| 6,719,760 B2 | 4/2004 | Dorchak et al. |
| 6,719,796 B2 | 4/2004 | Cohen et al. |
| 6,723,096 B1 | 4/2004 | Dorchak et al. |
| 6,723,126 B1 | 4/2004 | Berry |
| 6,730,126 B2 | 5/2004 | Boehm et al. |
| 6,733,532 B1 | 5/2004 | Gauchet et al. |
| 6,733,534 B2 | 5/2004 | Sherman |
| 6,733,535 B2 | 5/2004 | Michelson |
| 6,733,635 B1 | 5/2004 | Ozawa et al. |
| 6,740,090 B1 | 5/2004 | Cragg et al. |
| 6,740,093 B2 | 5/2004 | Hochschuler et al. |
| 6,740,117 B2 | 5/2004 | Ralph et al. |
| 6,743,166 B2 | 6/2004 | Berci et al. |
| 6,743,255 B2 | 6/2004 | Ferree |
| 6,746,451 B2 | 6/2004 | Middleton et al. |
| 6,752,831 B2 | 6/2004 | Sybert et al. |
| 6,761,720 B1 | 7/2004 | Senegas |
| 6,770,075 B2 | 8/2004 | Howland |
| 6,773,460 B2 | 8/2004 | Jackson |
| 6,790,210 B1 | 9/2004 | Cragg et al. |
| 6,793,656 B1 | 9/2004 | Mathews |
| 6,793,678 B2 | 9/2004 | Hawkins |
| 6,796,983 B1 | 9/2004 | Zucherman et al. |
| 6,805,685 B2 | 10/2004 | Taylor |
| 6,805,695 B2 | 10/2004 | Keith et al. |
| 6,805,714 B2 | 10/2004 | Sutcliffe |
| 6,808,526 B1 | 10/2004 | Magerl et al. |
| 6,808,537 B2 | 10/2004 | Michelson |
| 6,821,298 B1 | 11/2004 | Jackson |
| 6,830,589 B2 | 12/2004 | Erickson |
| 6,835,205 B2 | 12/2004 | Atkinson et al. |
| 6,835,206 B2 | 12/2004 | Jackson |
| 6,852,129 B2 | 2/2005 | Gerbec et al. |
| 6,855,167 B2 | 2/2005 | Shimp et al. |
| 6,863,673 B2 | 3/2005 | Gerbec et al. |
| 6,875,215 B2 | 4/2005 | Taras et al. |
| 6,881,229 B2 | 4/2005 | Khandkar et al. |
| 6,887,243 B2 | 5/2005 | Culbert |
| 6,890,333 B2 | 5/2005 | Von et al. |
| 6,893,464 B2 | 5/2005 | Kiester |
| 6,893,466 B2 | 5/2005 | Trieu |
| 6,902,566 B2 | 6/2005 | Zucherman et al. |
| 6,908,465 B2 | 6/2005 | Von et al. |
| 6,916,323 B2 | 7/2005 | Kitchens |

(56) References Cited

U.S. PATENT DOCUMENTS

| | | |
|---|---|---|
| 6,921,403 B2 | 7/2005 | Cragg et al. |
| 6,923,811 B1 | 8/2005 | Carl et al. |
| 6,929,606 B2 | 8/2005 | Ritland |
| 6,936,071 B1 | 8/2005 | Marnay et al. |
| 6,936,072 B2 | 8/2005 | Lambrecht et al. |
| 6,942,668 B2 | 9/2005 | Padget et al. |
| 6,945,975 B2 | 9/2005 | Dalton |
| 6,946,000 B2 | 9/2005 | Senegas et al. |
| 6,949,100 B1 | 9/2005 | Venturini |
| 6,951,561 B2 | 10/2005 | Warren et al. |
| 6,953,477 B2 | 10/2005 | Berry |
| 6,955,691 B2 | 10/2005 | Chae et al. |
| 6,969,404 B2 | 11/2005 | Ferree |
| 6,969,405 B2 | 11/2005 | Suddaby |
| 6,972,035 B2 | 12/2005 | Michelson |
| 6,997,929 B2 | 2/2006 | Manzi et al. |
| 7,004,945 B2 | 2/2006 | Boyd et al. |
| 7,008,431 B2 | 3/2006 | Simonson |
| 7,018,412 B2 | 3/2006 | Ferreira et al. |
| 7,018,415 B1 | 3/2006 | McKay |
| 7,018,416 B2 | 3/2006 | Hanson et al. |
| 7,025,746 B2 | 4/2006 | Tal |
| 7,029,473 B2 | 4/2006 | Zucherman et al. |
| 7,037,339 B2 | 5/2006 | Houfburg |
| 7,041,107 B2 | 5/2006 | Pohjonen et al. |
| 7,048,736 B2 | 5/2006 | Robinson et al. |
| 7,060,068 B2 | 6/2006 | Tromanhauser et al. |
| 7,063,701 B2 | 6/2006 | Michelson |
| 7,063,702 B2 | 6/2006 | Michelson |
| 7,066,960 B1 | 6/2006 | Dickman |
| 7,066,961 B2 | 6/2006 | Michelson |
| 7,070,601 B2 | 7/2006 | Culbert et al. |
| 7,074,203 B1 | 7/2006 | Johanson et al. |
| 7,083,650 B2 | 8/2006 | Moskowitz et al. |
| 7,087,083 B2 | 8/2006 | Pasquet et al. |
| 7,094,239 B1 | 8/2006 | Michelson |
| 7,094,257 B2 | 8/2006 | Mujwid et al. |
| 7,094,258 B2 | 8/2006 | Lambrecht et al. |
| 7,101,375 B2 | 9/2006 | Zucherman et al. |
| 7,114,501 B2 | 10/2006 | Johnson et al. |
| 7,118,572 B2 | 10/2006 | Bramlet et al. |
| 7,118,579 B2 | 10/2006 | Michelson |
| 7,118,598 B2 | 10/2006 | Michelson |
| 7,128,760 B2 | 10/2006 | Michelson |
| 7,153,305 B2 | 12/2006 | Johnson et al. |
| D536,096 S | 1/2007 | Hoogland et al. |
| 7,156,876 B2 | 1/2007 | Moumene et al. |
| 7,163,558 B2 | 1/2007 | Senegas et al. |
| 7,172,612 B2 | 2/2007 | Ishikawa |
| 7,179,294 B2 | 2/2007 | Eisermann et al. |
| 7,201,751 B2 | 4/2007 | Zucherman et al. |
| 7,211,112 B2 | 5/2007 | Baynham et al. |
| 7,217,293 B2 | 5/2007 | Branch, Jr. |
| 7,220,280 B2 | 5/2007 | Kast et al. |
| 7,223,292 B2 | 5/2007 | Messerli et al. |
| 7,226,481 B2 | 6/2007 | Kuslich |
| 7,226,483 B2 | 6/2007 | Gerber et al. |
| 7,235,101 B2 | 6/2007 | Berry et al. |
| 7,237,424 B2 | 7/2007 | Crutchley |
| 7,238,204 B2 | 7/2007 | Le et al. |
| 7,250,060 B2 | 7/2007 | Trieu |
| 7,267,683 B2 | 9/2007 | Sharkey et al. |
| 7,282,061 B2 | 10/2007 | Sharkey et al. |
| 7,300,440 B2 | 11/2007 | Zdeblick et al. |
| 7,306,628 B2 | 12/2007 | Zucherman et al. |
| 7,309,357 B2 | 12/2007 | Kim |
| 7,326,211 B2 | 2/2008 | Padget et al. |
| 7,326,248 B2 | 2/2008 | Michelson |
| 7,335,203 B2 | 2/2008 | Winslow et al. |
| 7,361,140 B2 | 4/2008 | Ries et al. |
| 7,371,238 B2 | 5/2008 | Soboleski et al. |
| 7,377,942 B2 | 5/2008 | Berry |
| 7,400,930 B2 | 7/2008 | Sharkey et al. |
| 7,410,501 B2 | 8/2008 | Michelson |
| 7,413,576 B2 | 8/2008 | Sybert et al. |
| 7,422,594 B2 | 9/2008 | Zander |
| 7,434,325 B2 | 10/2008 | Foley et al. |
| 7,445,637 B2 | 11/2008 | Taylor |
| D584,812 S | 1/2009 | Ries |
| 7,473,256 B2 | 1/2009 | Assell et al. |
| 7,473,268 B2 | 1/2009 | Zucherman et al. |
| 7,476,251 B2 | 1/2009 | Zucherman et al. |
| 7,488,326 B2 | 2/2009 | Elliott |
| 7,503,933 B2 | 3/2009 | Michelson |
| 7,507,241 B2 | 3/2009 | Levy et al. |
| 7,517,363 B2 | 4/2009 | Rogers et al. |
| 7,520,888 B2 | 4/2009 | Trieu |
| 7,547,317 B2 | 6/2009 | Cragg |
| 7,556,629 B2 | 7/2009 | Von et al. |
| 7,556,651 B2 | 7/2009 | Humphreys et al. |
| 7,569,074 B2 | 8/2009 | Eisermann et al. |
| 7,588,574 B2 | 9/2009 | Assell et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,625,378 B2 | 12/2009 | Foley |
| 7,641,657 B2 | 1/2010 | Cragg |
| 7,641,670 B2 | 1/2010 | Davison et al. |
| 7,647,123 B2 | 1/2010 | Sharkey et al. |
| 7,648,523 B2 | 1/2010 | Mirkovic et al. |
| 7,670,354 B2 | 3/2010 | Davison et al. |
| 7,674,273 B2 | 3/2010 | Davison et al. |
| 7,682,370 B2 | 3/2010 | Pagliuca et al. |
| 7,691,120 B2 | 4/2010 | Shluzas et al. |
| 7,691,147 B2 | 4/2010 | Guetlin et al. |
| 7,699,878 B2 | 4/2010 | Pavlov et al. |
| 7,703,727 B2 | 4/2010 | Selness |
| 7,717,944 B2 | 5/2010 | Foley et al. |
| 7,722,530 B2 | 5/2010 | Davison |
| 7,722,612 B2 | 5/2010 | Sala et al. |
| 7,722,674 B1 | 5/2010 | Grotz |
| 7,727,263 B2 | 6/2010 | Cragg |
| 7,740,633 B2 | 6/2010 | Assell et al. |
| 7,744,599 B2 | 6/2010 | Cragg |
| 7,749,270 B2 | 7/2010 | Peterman |
| 7,762,995 B2 | 7/2010 | Eversull et al. |
| 7,763,025 B2 | 7/2010 | Ainsworth |
| 7,763,055 B2 | 7/2010 | Foley |
| 7,766,930 B2 | 8/2010 | Dipoto et al. |
| 7,771,473 B2 | 8/2010 | Thramann |
| 7,771,479 B2 | 8/2010 | Humphreys et al. |
| 7,785,368 B2 | 8/2010 | Schaller |
| 7,789,914 B2 | 9/2010 | Michelson |
| 7,794,463 B2 | 9/2010 | Cragg |
| 7,799,032 B2 | 9/2010 | Assell et al. |
| 7,799,033 B2 | 9/2010 | Assell et al. |
| 7,799,036 B2 | 9/2010 | Davison et al. |
| D626,233 S | 10/2010 | Cipoletti et al. |
| 7,814,429 B2 | 10/2010 | Buffet et al. |
| 7,819,921 B2 | 10/2010 | Grotz |
| 7,824,410 B2 | 11/2010 | Simonson et al. |
| 7,824,429 B2 | 11/2010 | Culbert et al. |
| 7,824,445 B2 | 11/2010 | Biro et al. |
| 7,837,734 B2 | 11/2010 | Zucherman et al. |
| 7,846,183 B2 | 12/2010 | Blain |
| 7,846,206 B2 | 12/2010 | Oglaza et al. |
| 7,850,695 B2 | 12/2010 | Pagliuca et al. |
| 7,850,733 B2 | 12/2010 | Baynham et al. |
| 7,854,766 B2 | 12/2010 | Moskowitz et al. |
| 7,857,832 B2 | 12/2010 | Culbert et al. |
| 7,862,590 B2 | 1/2011 | Lim et al. |
| 7,862,595 B2 | 1/2011 | Foley et al. |
| 7,867,259 B2 | 1/2011 | Foley et al. |
| 7,874,980 B2 | 1/2011 | Sonnenschein et al. |
| 7,875,077 B2 | 1/2011 | Humphreys et al. |
| 7,879,098 B1 | 2/2011 | Simmons, Jr. |
| 7,887,589 B2 | 2/2011 | Glenn et al. |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,909,870 B2 | 3/2011 | Kraus |
| 7,922,729 B2 | 4/2011 | Michelson |
| 7,931,689 B2 | 4/2011 | Hochschuler et al. |

(56) References Cited

U.S. PATENT DOCUMENTS

| | | |
|---|---|---|
| 7,938,832 B2 | 5/2011 | Culbert et al. |
| 7,951,199 B2 | 5/2011 | Miller |
| 7,985,231 B2 | 7/2011 | Sankaran |
| 7,993,403 B2 | 8/2011 | Foley et al. |
| 7,998,176 B2 | 8/2011 | Culbert |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,043,381 B2 | 10/2011 | Hestad et al. |
| 8,062,375 B2 | 11/2011 | Glerum et al. |
| 8,075,621 B2 | 12/2011 | Michelson |
| 8,105,382 B2 | 1/2012 | Olmos et al. |
| 8,109,977 B2 | 2/2012 | Culbert et al. |
| 8,118,871 B2 | 2/2012 | Gordon |
| 8,128,700 B2 | 3/2012 | Delurio et al. |
| 8,133,232 B2 | 3/2012 | Levy et al. |
| 8,177,812 B2 | 5/2012 | Sankaran |
| 8,192,495 B2 | 6/2012 | Simpson et al. |
| 8,221,501 B2 | 7/2012 | Eisermann et al. |
| 8,221,502 B2 | 7/2012 | Branch, Jr. |
| 8,221,503 B2 | 7/2012 | Garcia et al. |
| 8,231,681 B2 | 7/2012 | Castleman et al. |
| 8,236,058 B2 | 8/2012 | Fabian et al. |
| 8,241,358 B2 | 8/2012 | Butler et al. |
| 8,257,440 B2 | 9/2012 | Gordon et al. |
| 8,257,442 B2 | 9/2012 | Edie et al. |
| 8,262,666 B2 | 9/2012 | Baynham et al. |
| 8,262,736 B2 | 9/2012 | Michelson |
| 8,267,939 B2 | 9/2012 | Cipoletti et al. |
| 8,273,128 B2 | 9/2012 | Oh et al. |
| 8,273,129 B2 | 9/2012 | Baynham et al. |
| 8,287,599 B2 | 10/2012 | McGuckin, Jr. |
| 8,303,663 B2 | 11/2012 | Jimenez et al. |
| 8,317,866 B2 | 11/2012 | Palmatier et al. |
| 8,323,345 B2 | 12/2012 | Sledge |
| 8,328,852 B2 | 12/2012 | Zehavi et al. |
| 8,337,559 B2 | 12/2012 | Hansell et al. |
| 8,353,961 B2 | 1/2013 | McClintock et al. |
| 8,366,777 B2 | 2/2013 | Matthis et al. |
| 8,382,842 B2 | 2/2013 | Greenhalgh et al. |
| 8,394,129 B2 | 3/2013 | Morgenstern et al. |
| 8,398,713 B2 | 3/2013 | Weiman |
| 8,403,990 B2 | 3/2013 | Dryer et al. |
| 8,409,291 B2 | 4/2013 | Blackwell et al. |
| 8,435,298 B2 | 5/2013 | Weiman |
| 8,454,617 B2 | 6/2013 | Schaller et al. |
| 8,486,148 B2 | 7/2013 | Butler et al. |
| 8,491,657 B2 | 7/2013 | Attia et al. |
| 8,491,659 B2 | 7/2013 | Weiman |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,535,380 B2 | 9/2013 | Greenhalgh et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim et al. |
| 8,591,585 B2 | 11/2013 | McLaughlin et al. |
| 8,597,333 B2 | 12/2013 | Morgenstern et al. |
| 8,603,170 B2 | 12/2013 | Cipoletti et al. |
| 8,623,091 B2 | 1/2014 | Suedkamp et al. |
| 8,628,576 B2 | 1/2014 | Triplett et al. |
| 8,628,578 B2 | 1/2014 | Miller et al. |
| 8,632,595 B2 | 1/2014 | Weiman |
| 8,663,329 B2 | 3/2014 | Ernst |
| 8,668,740 B2 | 3/2014 | Rhoda et al. |
| 8,679,183 B2 | 3/2014 | Glerum et al. |
| 8,685,098 B2 | 4/2014 | Glerum et al. |
| 8,696,751 B2 | 4/2014 | Ashley et al. |
| 8,709,086 B2 | 4/2014 | Glerum |
| 8,715,351 B1 | 5/2014 | Pinto |
| 8,721,723 B2 | 5/2014 | Hansell et al. |
| 8,728,160 B2 | 5/2014 | Globerman et al. |
| 8,753,398 B2 | 6/2014 | Gordon et al. |
| 8,771,360 B2 | 7/2014 | Jimenez et al. |
| 8,778,025 B2 | 7/2014 | Ragab et al. |
| 8,795,366 B2 | 8/2014 | Varela |
| 8,828,085 B1 | 9/2014 | Jensen |
| 8,845,731 B2 | 9/2014 | Weiman |
| 8,845,732 B2 | 9/2014 | Weiman |
| 8,845,734 B2 | 9/2014 | Weiman |
| 8,852,242 B2 | 10/2014 | Morgenstern et al. |
| 8,852,243 B2 | 10/2014 | Morgenstern et al. |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,307 B2 | 12/2014 | Hawkins et al. |
| 8,926,704 B2 | 1/2015 | Glerum et al. |
| 8,936,641 B2 | 1/2015 | Cain |
| 8,940,052 B2 | 1/2015 | Lechmann et al. |
| 8,974,508 B2 | 3/2015 | Stephan et al. |
| 8,979,860 B2 | 3/2015 | Voellmicke et al. |
| 8,986,387 B1 | 3/2015 | To et al. |
| 9,005,291 B2 | 4/2015 | Loebl et al. |
| 9,039,767 B2 | 5/2015 | Raymond et al. |
| 9,039,771 B2 | 5/2015 | Glerum et al. |
| 9,060,876 B1 | 6/2015 | To et al. |
| 9,078,767 B1 | 7/2015 | McLean |
| 9,095,446 B2 | 8/2015 | Landry et al. |
| 9,095,447 B2 | 8/2015 | Barreiro et al. |
| 9,101,488 B2 | 8/2015 | Malandain |
| 9,101,489 B2 | 8/2015 | Protopsaltis et al. |
| 9,107,766 B1 | 8/2015 | McLean et al. |
| 9,277,928 B2 | 3/2016 | Morgenstern Lopez |
| 9,295,562 B2 | 3/2016 | Lechmann et al. |
| 9,402,739 B2 | 8/2016 | Weiman et al. |
| 9,414,934 B2 | 8/2016 | Cain |
| 9,433,510 B2 | 9/2016 | Lechmann et al. |
| 9,463,099 B2 | 10/2016 | Levy et al. |
| 9,510,954 B2 | 12/2016 | Glerum et al. |
| 9,597,197 B2 | 3/2017 | Lechmann et al. |
| 9,833,334 B2 | 12/2017 | Voellmicke et al. |
| 2001/0012950 A1 | 8/2001 | Nishtala et al. |
| 2001/0027320 A1 | 10/2001 | Sasso |
| 2001/0037126 A1 | 11/2001 | Stack et al. |
| 2001/0039452 A1 | 11/2001 | Zucherman et al. |
| 2001/0049529 A1 | 12/2001 | Cachia et al. |
| 2001/0049530 A1 | 12/2001 | Culbert et al. |
| 2002/0001476 A1 | 1/2002 | Nagamine et al. |
| 2002/0010070 A1 | 1/2002 | Cales et al. |
| 2002/0032462 A1 | 3/2002 | Houser et al. |
| 2002/0037799 A1 | 3/2002 | Li et al. |
| 2002/0055740 A1 | 5/2002 | Lieberman |
| 2002/0068976 A1 | 6/2002 | Jackson |
| 2002/0068977 A1 | 6/2002 | Jackson |
| 2002/0087152 A1 | 7/2002 | Mikus et al. |
| 2002/0091387 A1 | 7/2002 | Hoogland |
| 2002/0120335 A1 | 8/2002 | Angelucci et al. |
| 2002/0128715 A1 | 9/2002 | Bryan et al. |
| 2002/0128716 A1 | 9/2002 | Cohen et al. |
| 2002/0138146 A1 | 9/2002 | Jackson |
| 2002/0143331 A1 | 10/2002 | Zucherman et al. |
| 2002/0143334 A1 | 10/2002 | Hoffmann et al. |
| 2002/0143335 A1 | 10/2002 | Von et al. |
| 2002/0151895 A1 | 10/2002 | Soboleski et al. |
| 2002/0151976 A1 | 10/2002 | Foley et al. |
| 2002/0161444 A1 | 10/2002 | Choi |
| 2002/0165612 A1 | 11/2002 | Gerber et al. |
| 2002/0183848 A1 | 12/2002 | Ray et al. |
| 2003/0004575 A1 | 1/2003 | Erickson |
| 2003/0004576 A1 | 1/2003 | Thalgott |
| 2003/0023305 A1 | 1/2003 | McKay |
| 2003/0028250 A1 | 2/2003 | Reiley et al. |
| 2003/0040799 A1 | 2/2003 | Boyd et al. |
| 2003/0063582 A1 | 4/2003 | Mizell et al. |
| 2003/0065330 A1 | 4/2003 | Zucherman et al. |
| 2003/0065396 A1 | 4/2003 | Michelson |
| 2003/0069582 A1 | 4/2003 | Culbert |
| 2003/0074063 A1 | 4/2003 | Gerbec et al. |
| 2003/0078667 A1 | 4/2003 | Manasas et al. |
| 2003/0083688 A1 | 5/2003 | Simonson |

(56) References Cited

U.S. PATENT DOCUMENTS

| | | |
|---|---|---|
| 2003/0130739 A1 | 7/2003 | Gerbec et al. |
| 2003/0135275 A1 | 7/2003 | Garcia et al. |
| 2003/0139648 A1 | 7/2003 | Foley et al. |
| 2003/0139812 A1 | 7/2003 | Garcia et al. |
| 2003/0139813 A1 | 7/2003 | Messerli et al. |
| 2003/0153874 A1 | 8/2003 | Tal |
| 2003/0187431 A1 | 10/2003 | Simonson |
| 2003/0208122 A1 | 11/2003 | Melkent et al. |
| 2003/0208220 A1 | 11/2003 | Worley et al. |
| 2003/0220643 A1 | 11/2003 | Ferree |
| 2003/0229350 A1 | 12/2003 | Kay |
| 2003/0233102 A1 | 12/2003 | Nakamura et al. |
| 2003/0233145 A1 | 12/2003 | Landry et al. |
| 2004/0006391 A1 | 1/2004 | Reiley |
| 2004/0008949 A1 | 1/2004 | Liu et al. |
| 2004/0019359 A1 | 1/2004 | Worley et al. |
| 2004/0024463 A1 | 2/2004 | Thomas et al. |
| 2004/0030387 A1 | 2/2004 | Landry et al. |
| 2004/0049190 A1 | 3/2004 | Biedermann et al. |
| 2004/0049223 A1 | 3/2004 | Nishtala et al. |
| 2004/0054412 A1 | 3/2004 | Gerbec et al. |
| 2004/0059339 A1 | 3/2004 | Roehm et al. |
| 2004/0059350 A1 | 3/2004 | Gordon et al. |
| 2004/0064144 A1 | 4/2004 | Johnson et al. |
| 2004/0087947 A1 | 5/2004 | Lim et al. |
| 2004/0088055 A1 | 5/2004 | Hanson et al. |
| 2004/0093083 A1 | 5/2004 | Branch et al. |
| 2004/0097924 A1 | 5/2004 | Lambrecht et al. |
| 2004/0097941 A1 | 5/2004 | Weiner et al. |
| 2004/0097973 A1 | 5/2004 | Loshakove et al. |
| 2004/0106925 A1 | 6/2004 | Culbert |
| 2004/0127906 A1 | 7/2004 | Culbert et al. |
| 2004/0127991 A1 | 7/2004 | Ferree |
| 2004/0133280 A1 | 7/2004 | Trieu |
| 2004/0143284 A1 | 7/2004 | Chin |
| 2004/0143734 A1 | 7/2004 | Buer et al. |
| 2004/0147877 A1 | 7/2004 | Heuser |
| 2004/0147950 A1 | 7/2004 | Mueller et al. |
| 2004/0148027 A1 | 7/2004 | Errico et al. |
| 2004/0153065 A1 | 8/2004 | Lim |
| 2004/0153156 A1 | 8/2004 | Cohen et al. |
| 2004/0153160 A1* | 8/2004 | Carrasco .............. A61F 2/44  623/17.15 |
| 2004/0158258 A1 | 8/2004 | Bonati et al. |
| 2004/0162617 A1 | 8/2004 | Zucherman et al. |
| 2004/0162618 A1 | 8/2004 | Mujwid et al. |
| 2004/0172133 A1 | 9/2004 | Gerber et al. |
| 2004/0172134 A1 | 9/2004 | Berry |
| 2004/0186471 A1 | 9/2004 | Trieu |
| 2004/0186482 A1 | 9/2004 | Kolb et al. |
| 2004/0186570 A1 | 9/2004 | Rapp |
| 2004/0186577 A1 | 9/2004 | Ferree |
| 2004/0199162 A1 | 10/2004 | Von et al. |
| 2004/0215343 A1 | 10/2004 | Hochschuler et al. |
| 2004/0215344 A1 | 10/2004 | Hochschuler et al. |
| 2004/0220580 A1 | 11/2004 | Johnson et al. |
| 2004/0225292 A1 | 11/2004 | Sasso et al. |
| 2004/0225361 A1 | 11/2004 | Glenn et al. |
| 2004/0230309 A1 | 11/2004 | Dimauro et al. |
| 2004/0243239 A1 | 12/2004 | Taylor |
| 2004/0249466 A1 | 12/2004 | Liu et al. |
| 2004/0254575 A1 | 12/2004 | Obenchain et al. |
| 2004/0260297 A1 | 12/2004 | Padget et al. |
| 2004/0266257 A1 | 12/2004 | Ries et al. |
| 2005/0033289 A1 | 2/2005 | Warren et al. |
| 2005/0033434 A1 | 2/2005 | Berry |
| 2005/0038515 A1 | 2/2005 | Kunzler |
| 2005/0043796 A1 | 2/2005 | Grant et al. |
| 2005/0065610 A1 | 3/2005 | Pisharodi |
| 2005/0090443 A1 | 4/2005 | Michael John |
| 2005/0090833 A1 | 4/2005 | Dipoto |
| 2005/0102202 A1 | 5/2005 | Linden et al. |
| 2005/0113916 A1 | 5/2005 | Branch, Jr. |
| 2005/0113917 A1 | 5/2005 | Chae et al. |
| 2005/0113927 A1 | 5/2005 | Malek |
| 2005/0118550 A1 | 6/2005 | Turri |
| 2005/0119657 A1 | 6/2005 | Goldsmith |
| 2005/0125062 A1 | 6/2005 | Biedermann et al. |
| 2005/0130929 A1 | 6/2005 | Boyd |
| 2005/0131406 A1 | 6/2005 | Reiley et al. |
| 2005/0131409 A1 | 6/2005 | Chervitz et al. |
| 2005/0131411 A1 | 6/2005 | Culbert |
| 2005/0131538 A1 | 6/2005 | Chervitz et al. |
| 2005/0137595 A1 | 6/2005 | Hoffmann et al. |
| 2005/0143734 A1 | 6/2005 | Cachia et al. |
| 2005/0149030 A1 | 7/2005 | Serhan et al. |
| 2005/0154467 A1 | 7/2005 | Peterman et al. |
| 2005/0165398 A1 | 7/2005 | Reiley |
| 2005/0165485 A1 | 7/2005 | Trieu |
| 2005/0171552 A1 | 8/2005 | Johnson et al. |
| 2005/0171608 A1 | 8/2005 | Peterman et al. |
| 2005/0171610 A1 | 8/2005 | Humphreys et al. |
| 2005/0177235 A1 | 8/2005 | Baynham et al. |
| 2005/0177240 A1 | 8/2005 | Blain |
| 2005/0182414 A1 | 8/2005 | Manzi et al. |
| 2005/0182418 A1 | 8/2005 | Boyd et al. |
| 2005/0187558 A1 | 8/2005 | Johnson et al. |
| 2005/0187559 A1 | 8/2005 | Raymond et al. |
| 2005/0203512 A1 | 9/2005 | Hawkins et al. |
| 2005/0216026 A1 | 9/2005 | Culbert |
| 2005/0222681 A1 | 10/2005 | Richley et al. |
| 2005/0251142 A1 | 11/2005 | Hoffmann et al. |
| 2005/0256525 A1 | 11/2005 | Culbert et al. |
| 2005/0256576 A1 | 11/2005 | Moskowitz et al. |
| 2005/0261769 A1 | 11/2005 | Moskowitz et al. |
| 2005/0278026 A1 | 12/2005 | Gordon et al. |
| 2005/0283238 A1 | 12/2005 | Reiley |
| 2006/0004326 A1 | 1/2006 | Collins et al. |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0015105 A1 | 1/2006 | Warren et al. |
| 2006/0020284 A1 | 1/2006 | Foley et al. |
| 2006/0030872 A1 | 2/2006 | Culbert et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0041314 A1 | 2/2006 | Millard |
| 2006/0058790 A1 | 3/2006 | Carl et al. |
| 2006/0058807 A1 | 3/2006 | Landry et al. |
| 2006/0058876 A1 | 3/2006 | McKinley |
| 2006/0058880 A1 | 3/2006 | Wysocki et al. |
| 2006/0079908 A1 | 4/2006 | Lieberman |
| 2006/0084977 A1 | 4/2006 | Lieberman |
| 2006/0084988 A1 | 4/2006 | Kim |
| 2006/0085010 A1 | 4/2006 | Lieberman |
| 2006/0100706 A1 | 5/2006 | Shadduck et al. |
| 2006/0100707 A1 | 5/2006 | Stinson et al. |
| 2006/0106381 A1 | 5/2006 | Ferree et al. |
| 2006/0119629 A1 | 6/2006 | An et al. |
| 2006/0122609 A1 | 6/2006 | Mirkovic et al. |
| 2006/0122610 A1 | 6/2006 | Culbert et al. |
| 2006/0122701 A1 | 6/2006 | Kiester |
| 2006/0122703 A1 | 6/2006 | Aebi et al. |
| 2006/0129244 A1 | 6/2006 | Ensign |
| 2006/0136062 A1 | 6/2006 | Dinello et al. |
| 2006/0142759 A1 | 6/2006 | Amin et al. |
| 2006/0142765 A9 | 6/2006 | Dixon et al. |
| 2006/0142776 A1 | 6/2006 | Iwanari |
| 2006/0142858 A1 | 6/2006 | Colleran et al. |
| 2006/0161166 A1 | 7/2006 | Johnson et al. |
| 2006/0178743 A1 | 8/2006 | Carter |
| 2006/0195103 A1 | 8/2006 | Padget et al. |
| 2006/0206207 A1 | 9/2006 | Dryer et al. |
| 2006/0215343 A1 | 9/2006 | Camagna et al. |
| 2006/0217711 A1 | 9/2006 | Stevens et al. |
| 2006/0229629 A1 | 10/2006 | Manzi et al. |
| 2006/0235403 A1 | 10/2006 | Blain |
| 2006/0235412 A1 | 10/2006 | Blain |
| 2006/0235531 A1 | 10/2006 | Buettner-Janz |

(56) References Cited

U.S. PATENT DOCUMENTS

| | | |
|---|---|---|
| 2006/0247634 A1 | 11/2006 | Warner et al. |
| 2006/0253201 A1 | 11/2006 | McLuen |
| 2006/0265075 A1 | 11/2006 | Baumgartner et al. |
| 2006/0265077 A1 | 11/2006 | Zwirkoski |
| 2006/0276899 A1 | 12/2006 | Zipnick et al. |
| 2006/0276901 A1 | 12/2006 | Zipnick et al. |
| 2006/0276902 A1 | 12/2006 | Zipnick et al. |
| 2006/0293662 A1 | 12/2006 | Boyer et al. |
| 2006/0293663 A1 | 12/2006 | Walkenhorst et al. |
| 2007/0010826 A1 | 1/2007 | Rhoda et al. |
| 2007/0010886 A1 | 1/2007 | Banick et al. |
| 2007/0016191 A1 | 1/2007 | Culbert et al. |
| 2007/0032790 A1 | 2/2007 | Aschmann et al. |
| 2007/0055236 A1 | 3/2007 | Hudgins et al. |
| 2007/0055377 A1 | 3/2007 | Hanson et al. |
| 2007/0067035 A1 | 3/2007 | Falahee |
| 2007/0073399 A1 | 3/2007 | Zipnick et al. |
| 2007/0118132 A1 | 5/2007 | Culbert et al. |
| 2007/0118222 A1 | 5/2007 | Lang |
| 2007/0118223 A1 | 5/2007 | Allard et al. |
| 2007/0123868 A1 | 5/2007 | Culbert et al. |
| 2007/0123891 A1 | 5/2007 | Ries et al. |
| 2007/0123892 A1 | 5/2007 | Ries et al. |
| 2007/0129730 A1 | 6/2007 | Woods et al. |
| 2007/0149978 A1 | 6/2007 | Shezifi et al. |
| 2007/0162005 A1 | 7/2007 | Peterson et al. |
| 2007/0162138 A1 | 7/2007 | Heinz |
| 2007/0168036 A1 | 7/2007 | Ainsworth et al. |
| 2007/0173939 A1 | 7/2007 | Kim et al. |
| 2007/0173940 A1 | 7/2007 | Hestad et al. |
| 2007/0191954 A1 | 8/2007 | Hansell et al. |
| 2007/0191959 A1 | 8/2007 | Hartmann et al. |
| 2007/0198089 A1 | 8/2007 | Moskowitz et al. |
| 2007/0203491 A1 | 8/2007 | Pasquet et al. |
| 2007/0208423 A1 | 9/2007 | Messerli et al. |
| 2007/0219634 A1 | 9/2007 | Greenhalgh et al. |
| 2007/0233083 A1 | 10/2007 | Abdou |
| 2007/0233089 A1 | 10/2007 | Dipoto et al. |
| 2007/0233244 A1 | 10/2007 | Lopez et al. |
| 2007/0270954 A1 | 11/2007 | Wu |
| 2007/0270968 A1 | 11/2007 | Baynham et al. |
| 2007/0276375 A1 | 11/2007 | Rapp |
| 2007/0282449 A1 | 12/2007 | De et al. |
| 2007/0299521 A1 | 12/2007 | Glenn et al. |
| 2008/0009877 A1 | 1/2008 | Sankaran et al. |
| 2008/0015701 A1 | 1/2008 | Garcia et al. |
| 2008/0021556 A1* | 1/2008 | Edie .......... A61F 2/44 623/17.11 |
| 2008/0021558 A1 | 1/2008 | Thramann |
| 2008/0027550 A1 | 1/2008 | Link et al. |
| 2008/0033440 A1 | 2/2008 | Moskowitz et al. |
| 2008/0058598 A1 | 3/2008 | Ries et al. |
| 2008/0058944 A1 | 3/2008 | Duplessis et al. |
| 2008/0065219 A1 | 3/2008 | Dye |
| 2008/0077148 A1 | 3/2008 | Ries et al. |
| 2008/0082172 A1 | 4/2008 | Jackson |
| 2008/0082173 A1 | 4/2008 | Delurio et al. |
| 2008/0097436 A1 | 4/2008 | Culbert et al. |
| 2008/0103601 A1 | 5/2008 | Biro et al. |
| 2008/0108996 A1 | 5/2008 | Padget et al. |
| 2008/0132934 A1 | 6/2008 | Reiley et al. |
| 2008/0140207 A1 | 6/2008 | Olmos et al. |
| 2008/0147193 A1 | 6/2008 | Matthis et al. |
| 2008/0154377 A1 | 6/2008 | Voellmicke |
| 2008/0161927 A1 | 7/2008 | Savage et al. |
| 2008/0167657 A1 | 7/2008 | Greenhalgh |
| 2008/0177388 A1 | 7/2008 | Patterson et al. |
| 2008/0183204 A1 | 7/2008 | Greenhalgh et al. |
| 2008/0195209 A1 | 8/2008 | Garcia et al. |
| 2008/0243251 A1 | 10/2008 | Stad et al. |
| 2008/0243254 A1 | 10/2008 | Butler |
| 2008/0249622 A1 | 10/2008 | Gray |
| 2008/0255618 A1 | 10/2008 | Fisher et al. |
| 2008/0262619 A1 | 10/2008 | Ray |
| 2008/0269904 A1 | 10/2008 | Voorhies |
| 2008/0281425 A1 | 11/2008 | Thalgott et al. |
| 2008/0287981 A1 | 11/2008 | Culbert et al. |
| 2008/0287997 A1 | 11/2008 | Altarac et al. |
| 2008/0300685 A1 | 12/2008 | Carls et al. |
| 2008/0306537 A1 | 12/2008 | Culbert |
| 2009/0005870 A1 | 1/2009 | Hawkins et al. |
| 2009/0005873 A1 | 1/2009 | Slivka et al. |
| 2009/0030423 A1 | 1/2009 | Puno |
| 2009/0048631 A1 | 2/2009 | Bhatnagar et al. |
| 2009/0054991 A1 | 2/2009 | Biyani et al. |
| 2009/0069813 A1 | 3/2009 | Von et al. |
| 2009/0076610 A1 | 3/2009 | Afzal |
| 2009/0099568 A1 | 4/2009 | Lowry et al. |
| 2009/0105712 A1 | 4/2009 | Dauster et al. |
| 2009/0105745 A1 | 4/2009 | Culbert |
| 2009/0112320 A1 | 4/2009 | Kraus |
| 2009/0112324 A1 | 4/2009 | Refai et al. |
| 2009/0131986 A1 | 5/2009 | Lee et al. |
| 2009/0149857 A1 | 6/2009 | Culbert et al. |
| 2009/0164020 A1 | 6/2009 | Janowski et al. |
| 2009/0177284 A1 | 7/2009 | Rogers et al. |
| 2009/0182429 A1 | 7/2009 | Humphreys et al. |
| 2009/0192614 A1 | 7/2009 | Beger et al. |
| 2009/0222096 A1 | 9/2009 | Trieu |
| 2009/0222099 A1 | 9/2009 | Liu et al. |
| 2009/0222100 A1 | 9/2009 | Cipoletti et al. |
| 2009/0234398 A1 | 9/2009 | Chirico et al. |
| 2009/0240335 A1 | 9/2009 | Arcenio et al. |
| 2009/0248159 A1 | 10/2009 | Aflatoon |
| 2009/0275890 A1 | 11/2009 | Leibowitz et al. |
| 2009/0281580 A1 | 11/2009 | Emannuel |
| 2009/0292361 A1 | 11/2009 | Lopez |
| 2010/0016905 A1 | 1/2010 | Greenhalgh et al. |
| 2010/0040332 A1 | 2/2010 | Van et al. |
| 2010/0076492 A1 | 3/2010 | Warner et al. |
| 2010/0076559 A1 | 3/2010 | Bagga et al. |
| 2010/0082109 A1 | 4/2010 | Greenhalgh et al. |
| 2010/0094424 A1 | 4/2010 | Woodburn et al. |
| 2010/0114105 A1 | 5/2010 | Butters et al. |
| 2010/0114147 A1 | 5/2010 | Biyani |
| 2010/0174314 A1 | 7/2010 | Mirkovic et al. |
| 2010/0179594 A1 | 7/2010 | Theofilos et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0234956 A1 | 9/2010 | Attia et al. |
| 2010/0262240 A1 | 10/2010 | Chavatte et al. |
| 2010/0268231 A1 | 10/2010 | Kuslich et al. |
| 2010/0268338 A1 | 10/2010 | Melkent et al. |
| 2010/0286783 A1 | 11/2010 | Lechmann et al. |
| 2010/0292700 A1 | 11/2010 | Ries |
| 2010/0298938 A1 | 11/2010 | Humphreys et al. |
| 2010/0324607 A1 | 12/2010 | Davis |
| 2010/0331891 A1 | 12/2010 | Culbert et al. |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0054538 A1 | 3/2011 | Zehavi et al. |
| 2011/0071527 A1 | 3/2011 | Nelson et al. |
| 2011/0093074 A1 | 4/2011 | Glerum et al. |
| 2011/0098531 A1 | 4/2011 | To |
| 2011/0098628 A1 | 4/2011 | Yeung et al. |
| 2011/0130835 A1 | 6/2011 | Ashley et al. |
| 2011/0130838 A1 | 6/2011 | Morgenstern Lopez |
| 2011/0144692 A1 | 6/2011 | Saladin et al. |
| 2011/0144753 A1 | 6/2011 | Marchek et al. |
| 2011/0153020 A1 | 6/2011 | Abdelgany et al. |
| 2011/0172716 A1 | 7/2011 | Glerum |
| 2011/0172774 A1 | 7/2011 | Varela |
| 2011/0238072 A1 | 9/2011 | Tyndall |
| 2011/0270261 A1 | 11/2011 | Mast et al. |
| 2011/0270401 A1 | 11/2011 | McKay |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2011/0307010 A1 | 12/2011 | Pradhan |
| 2011/0313465 A1 | 12/2011 | Warren et al. |

(56) References Cited

U.S. PATENT DOCUMENTS

| | | |
|---|---|---|
| 2011/0320000 A1 | 12/2011 | O'Neil |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0059474 A1 | 3/2012 | Weiman |
| 2012/0059475 A1 | 3/2012 | Weiman |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0185049 A1 | 7/2012 | Varela |
| 2012/0197403 A1 | 8/2012 | Merves |
| 2012/0197405 A1 | 8/2012 | Cuevas et al. |
| 2012/0203290 A1 | 8/2012 | Warren et al. |
| 2012/0203347 A1 | 8/2012 | Glerum et al. |
| 2012/0215262 A1 | 8/2012 | Culbert et al. |
| 2012/0226357 A1 | 9/2012 | Varela |
| 2012/0232552 A1 | 9/2012 | Morgenstern et al. |
| 2012/0232658 A1 | 9/2012 | Morgenstern et al. |
| 2012/0265309 A1 | 10/2012 | Glerum et al. |
| 2012/0277795 A1 | 11/2012 | Von et al. |
| 2012/0290090 A1 | 11/2012 | Glerum et al. |
| 2012/0290097 A1 | 11/2012 | Cipoletti et al. |
| 2012/0310350 A1 | 12/2012 | Farris et al. |
| 2012/0310352 A1 | 12/2012 | Dimauro et al. |
| 2012/0323328 A1 | 12/2012 | Weiman |
| 2012/0330421 A1 | 12/2012 | Weiman |
| 2012/0330422 A1 | 12/2012 | Weiman |
| 2013/0006361 A1 | 1/2013 | Glerum et al. |
| 2013/0023993 A1 | 1/2013 | Weiman |
| 2013/0023994 A1 | 1/2013 | Glerum |
| 2013/0030536 A1 | 1/2013 | Rhoda et al. |
| 2013/0085572 A1 | 4/2013 | Glerum et al. |
| 2013/0085574 A1 | 4/2013 | Sledge |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0310939 A1 | 11/2013 | Fabian et al. |
| 2014/0025169 A1 | 1/2014 | Lechmann et al. |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Hauck |
| 2014/0094916 A1 | 4/2014 | Glerum et al. |
| 2014/0100662 A1 | 4/2014 | Patterson |
| 2014/0114423 A1 | 4/2014 | Suedkamp et al. |
| 2014/0128977 A1 | 5/2014 | Glerum et al. |
| 2014/0135934 A1 | 5/2014 | Hansell et al. |
| 2014/0142706 A1 | 5/2014 | Hansell et al. |
| 2014/0163682 A1 | 6/2014 | Lott |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0228959 A1 | 8/2014 | Niemiec et al. |
| 2014/0236296 A1 | 8/2014 | Wagner et al. |
| 2014/0243981 A1 | 8/2014 | Davenport et al. |
| 2014/0243982 A1 | 8/2014 | Miller |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0277139 A1 | 9/2014 | Vrionis et al. |
| 2014/0277204 A1 | 9/2014 | Sandhu |
| 2014/0277474 A1 | 9/2014 | Robinson et al. |
| 2014/0303731 A1 | 10/2014 | Glerum |
| 2014/0303732 A1 | 10/2014 | Rhoda et al. |
| 2014/0324171 A1 | 10/2014 | Glerum et al. |
| 2015/0012097 A1 | 1/2015 | Ibarra et al. |
| 2015/0045894 A1 | 2/2015 | Hawkins et al. |
| 2015/0066145 A1 | 3/2015 | Rogers et al. |
| 2015/0094610 A1 | 4/2015 | Morgenstern et al. |
| 2015/0094812 A1 | 4/2015 | Cain |
| 2015/0094813 A1 | 4/2015 | Lechmann et al. |
| 2015/0100128 A1 | 4/2015 | Glerum et al. |
| 2015/0112398 A1 | 4/2015 | Morgenstern et al. |
| 2015/0112438 A1 | 4/2015 | McLean |
| 2015/0157470 A1 | 6/2015 | Voellmicke et al. |
| 2015/0173916 A1 | 6/2015 | Cain |
| 2015/0182347 A1 | 7/2015 | Robinson |
| 2015/0216671 A1 | 8/2015 | Cain |
| 2015/0216672 A1 | 8/2015 | Cain |
| 2015/0250606 A1 | 9/2015 | McLean |
| 2015/0320571 A1 | 11/2015 | Lechmann et al. |
| 2016/0045333 A1 | 2/2016 | Baynham |
| 2016/0081814 A1 | 3/2016 | Baynham |
| 2016/0089247 A1 | 3/2016 | Nichols et al. |
| 2016/0106551 A1 | 4/2016 | Grimberg et al. |
| 2016/0113776 A1 | 4/2016 | Capote |
| 2016/0242929 A1 | 8/2016 | Voellmicke et al. |
| 2016/0256291 A1 | 9/2016 | Miller |
| 2016/0317317 A1 | 11/2016 | Marchek et al. |
| 2016/0331546 A1 | 11/2016 | Lechmann et al. |
| 2016/0367265 A1 | 12/2016 | Morgenstern Lopez |
| 2017/0000622 A1 | 1/2017 | Thommen et al. |
| 2017/0100255 A1 | 4/2017 | Hleihil et al. |
| 2017/0290674 A1 | 10/2017 | Olmos et al. |

FOREIGN PATENT DOCUMENTS

| | | |
|---|---|---|
| CN | 101087566 A | 12/2007 |
| CN | 101631516 A | 1/2010 |
| CN | 101909548 A | 12/2010 |
| CN | 102164552 A | 8/2011 |
| DE | 2804936 A1 | 8/1979 |
| DE | 3023353 A1 | 4/1981 |
| DE | 3911610 A1 | 10/1990 |
| DE | 4012622 C1 | 7/1991 |
| DE | 19832798 C1 | 11/1999 |
| DE | 20101793 U1 | 5/2001 |
| DE | 202008001079 U1 | 3/2008 |
| EP | 0077159 A1 | 4/1983 |
| EP | 0260044 A1 | 3/1988 |
| EP | 0270704 A1 | 6/1988 |
| EP | 0282161 A1 | 9/1988 |
| EP | 0433717 A1 | 6/1991 |
| EP | 0525352 A1 | 2/1993 |
| EP | 0611557 A2 | 8/1994 |
| EP | 0625336 A2 | 11/1994 |
| EP | 0678489 A1 | 10/1995 |
| EP | 0853929 A2 | 7/1998 |
| EP | 1046376 A1 | 10/2000 |
| EP | 1290985 A2 | 3/2003 |
| EP | 1374784 A1 | 1/2004 |
| EP | 1378205 A1 | 1/2004 |
| EP | 1532949 A1 | 5/2005 |
| EP | 1541096 A1 | 6/2005 |
| EP | 1683593 A2 | 7/2006 |
| EP | 1698305 A1 | 9/2006 |
| EP | 1843723 A1 | 10/2007 |
| EP | 1845874 A1 | 10/2007 |
| EP | 2331023 A2 | 6/2011 |
| EP | 2368529 A1 | 9/2011 |
| EP | 2237748 B1 | 9/2012 |
| EP | 2764851 A1 | 8/2014 |

(56) References Cited

FOREIGN PATENT DOCUMENTS

| | | |
|---|---|---|
| FR | 2649311 A1 | 1/1991 |
| FR | 2699065 A1 | 6/1994 |
| FR | 2718635 A1 | 10/1995 |
| FR | 2728778 A1 | 7/1996 |
| FR | 2730159 A1 | 8/1996 |
| FR | 2745709 A1 | 9/1997 |
| FR | 2800601 A1 | 5/2001 |
| FR | 2801189 A1 | 5/2001 |
| FR | 2808182 A1 | 11/2001 |
| FR | 2874814 A1 | 3/2006 |
| GB | 2157788 A | 10/1985 |
| GB | 2173565 A | 10/1986 |
| JP | 64-052439 A | 2/1989 |
| JP | 06-500039 A | 1/1994 |
| JP | 06-319742 A | 11/1994 |
| JP | 07-502419 A | 3/1995 |
| JP | 07-184922 A | 7/1995 |
| JP | 10-085232 A | 4/1998 |
| JP | 11-089854 A | 4/1999 |
| JP | 2003-010197 A | 1/2003 |
| JP | 2003-126266 A | 5/2003 |
| JP | 2003-526457 A | 9/2003 |
| JP | 2006-516456 | 7/2006 |
| JP | 2007-054666 A | 3/2007 |
| JP | 2008-126085 A | 6/2008 |
| JP | 2011-509766 A | 3/2011 |
| JP | 2011-520580 A | 7/2011 |
| JP | 4988203 B2 | 8/2012 |
| JP | 5164571 B2 | 3/2013 |
| WO | 91/09572 A1 | 7/1991 |
| WO | 93/04652 A1 | 3/1993 |
| WO | 94/04100 A1 | 3/1994 |
| WO | 95/31158 | 11/1995 |
| WO | 96/28100 A1 | 9/1996 |
| WO | 97/00054 A1 | 1/1997 |
| WO | 99/42062 A1 | 8/1999 |
| WO | 99/52478 A1 | 10/1999 |
| WO | 99/53871 A1 | 10/1999 |
| WO | 99/62417 A1 | 12/1999 |
| WO | 00/12033 | 3/2000 |
| WO | 00/67652 | 5/2000 |
| WO | 00/53127 A1 | 9/2000 |
| WO | 00/74605 A1 | 12/2000 |
| WO | 00/76409 A1 | 12/2000 |
| WO | 01/01893 A1 | 1/2001 |
| WO | 01/01895 A1 | 1/2001 |
| WO | 01/12054 A2 | 2/2001 |
| WO | 01/17464 A1 | 3/2001 |
| WO | 01/68004 A2 | 9/2001 |
| WO | 01/80751 A1 | 11/2001 |
| WO | 02/43601 A2 | 6/2002 |
| WO | 03/21308 A2 | 3/2003 |
| WO | 03/43488 A2 | 5/2003 |
| WO | 2004/008949 A1 | 1/2004 |
| WO | 2004/064603 A2 | 8/2004 |
| WO | 2004/078220 A2 | 9/2004 |
| WO | 2004/078221 A2 | 9/2004 |
| WO | 2004/098453 A2 | 11/2004 |
| WO | 2005/112834 A2 | 12/2005 |
| WO | 2005/112835 A2 | 12/2005 |
| WO | 2006/017507 A2 | 2/2006 |
| WO | 2006/047587 A2 | 5/2006 |
| WO | 2006/058281 A2 | 6/2006 |
| WO | 2006/063083 A1 | 6/2006 |
| WO | 2006/065419 A2 | 6/2006 |
| WO | 2006/081843 A1 | 8/2006 |
| WO | 2006/108067 A2 | 10/2006 |
| WO | 2007/009107 A2 | 1/2007 |
| WO | 2007/028098 A2 | 3/2007 |
| WO | 2007/048012 A2 | 4/2007 |
| WO | 2007/119212 A2 | 10/2007 |
| WO | 2007/124130 A2 | 11/2007 |
| WO | 2008/044057 A1 | 4/2008 |
| WO | 2008/064842 A2 | 6/2008 |
| WO | 2008/070863 A2 | 6/2008 |
| WO | 2009/064787 A2 | 5/2009 |
| WO | 2009/092102 A1 | 7/2009 |
| WO | 2009/124269 A1 | 10/2009 |
| WO | 2009/143496 A1 | 11/2009 |
| WO | 2009/147527 A2 | 12/2009 |
| WO | 2009/152919 A1 | 12/2009 |
| WO | 2010/068725 A2 | 6/2010 |
| WO | 2010/136170 A1 | 12/2010 |
| WO | 2010/148112 A1 | 12/2010 |
| WO | 2011/079910 A2 | 7/2011 |
| WO | 2011/142761 A1 | 11/2011 |
| WO | 2011/150350 A1 | 12/2011 |
| WO | 2012/009152 A1 | 1/2012 |
| WO | 2012/089317 A1 | 7/2012 |
| WO | 2012/122294 A1 | 9/2012 |
| WO | 2012/135764 A1 | 10/2012 |
| WO | 2013/006669 A2 | 1/2013 |
| WO | 2013/023096 A1 | 2/2013 |
| WO | 2013/025876 A1 | 2/2013 |
| WO | 2013/043850 A2 | 3/2013 |
| WO | 2013/062903 A1 | 5/2013 |
| WO | 2013/082184 A1 | 6/2013 |
| WO | 2013/158294 A1 | 10/2013 |
| WO | 2013/173767 A1 | 11/2013 |
| WO | 2013/184946 A1 | 12/2013 |
| WO | 2014/018098 A1 | 1/2014 |
| WO | 2014/026007 A1 | 2/2014 |
| WO | 2014/035962 A1 | 3/2014 |
| WO | 2014/088521 A2 | 6/2014 |
| WO | 2014/116891 A1 | 7/2014 |
| WO | 2014/144696 A1 | 9/2014 |
| WO | 2016/069796 A1 | 5/2016 |
| WO | 2016/127139 A1 | 8/2016 |

OTHER PUBLICATIONS

U.S. Appl. No. 60/942,998, filed Jun. 8, 2007.
Talwar "Insertion loads of the X STOP interspinous process distraction system designed to treat neurogenic intermittent claudication", Eur Spine J. (2006) 15: pp. 908-912.
Spine Solutions Brochure—Prodisc 2001, 16 pages.
Siddiqui, "The Positional Magnetic Resonance Imaging Changes in the Lumbar Spine Following Insertion of a Novel Interspinous Process Distraction Device", Spine, vol. 30, No. 23, pp. 2677-2682, 2005.
Shin, "Posterior Lumbar Interbody Fusion via a Unilateral Approach", Yonsei Medical Journal, 2006, pp. 319-325, vol. 47(3).
ProMap TM EMG Navigation Probe. Technical Brochure Spineology Inc, Dated May 2009.
Polikeit, "The Importance of the Endplate for Interbody Cages in the Lumbar Spine", Eur. Spine J., 2003, pp. 556-561, vol. 12.
Niosi, Christina A., "Biomechanical Characterization of the three-dimentinoal kinematic behavior of the Dynesys dynamic stabilization system: an in vitro study", Eur Spine J. (2006) 15: pp. 913-922.
Morgenstern R; "Transforaminal Endoscopic Stenosis Surgery—A Comparative Study of Laser and Reamed Foraminoplasty", in European Musculoskeletal Review, Issue 1, 2009.
Method and Apparatus for Spinal Stabilization, U.S. Appl. No. 60/942,998.
Method and Apparatus for Spinal Fixation, U.S. Appl. No. 60/794,171.
Method and Apparatus for Spinal Fixation, U.S. Appl. No. 60/424,055.
Method and apparatus for spinal fixation, U.S. Appl. No. 60/397,588.
Medco Forum, "Percutaneous Lumbar Fixation via PERPOS System From Interventional Spine", Oct. 2007, vol. 14, No. 49.
Medco Forum, "Percutaneous Lumbar Fixation Via PERPOS PLS System Interventional Spine", Sep. 2008, vol. 15, No. 37.
Mahar et al., "Biomechanical Comparison of Novel Percutaneous Transfacet Device and a Traditional Posterior System for Single Level Fusion", Journal of Spinal Disorders & Techniques, Dec. 2006, vol. 19, No. 8, pp. 591-594.
Link SB Charite Brochure—Intervertebral Prosthesis 1988, 29 pages.
Krbec, "Replacement of the Vertebral Body with an Expansion Implant (Synex)", Acta Chir Orthop Traumatol Cech, 2002, pp. 158-162, vol. 69(3).

(56) References Cited

OTHER PUBLICATIONS

King, M.D., Don, "Internal Fixation for Lumbosacral Fusion, The Journal of Bone and Joint Surgery", J. Bone Joint Surg Am., 1948; 30: 560-578.

Kambin et al., "Percutaneous Lateral Discectomy of the Lumbar Spine: A Preliminary Report", Clin. Orthop,: 1983, 174: 127-132.

Iprenburg et al., "Transforaminal Endoscopic Surgery in Lumbar Disc Herniation in an Economic Crisis—The TESSYS Method", US Musculoskeletal, 2008, p. 47-49.

Hunt, "Expandable Cage Placement Via a Posterolateral Approach in Lumbar Spine Reconstructions", Journal of Neurosurgery: Spine, Sep. 2006, pp. 271-274, vol. 5.

Hoogland et al., "Total Lumar Intervertebral Disc Replacement: Testing a New Articulating Space in Human Cadaver Spines-24 1", Annual ORS, Dallas, TX, Feb. 21-23, 1978, 8 pages.

Gray's Anatomy, Crown Publishers, Inc., 1977, pp. 33-54.

Gore, "Technique of Cervical Interbody Fusion", Clinical Orthopaedics and Related Research, Sep. 1984, pp. 191-195, No. 188.

Fuchs, "The use of an interspinous implant in conjuction with a graded facetectomy procedure", Spine vol. 30, No. 11, pp. 1266-1272, 2005.

Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).

Expandable Intervertebral Implant, U.S. Appl. No. 14/685,402.

Expandable Intervertebral Implant, U.S. Appl. No. 14/685,358.

Expandable Intervertebral Implant, U.S. Appl. No. 14/640,220.

Expandable Implant, U.S. Appl. No. 61/675,975.

Expandable Implant, U.S. Appl. No. 14/790,866.

Chin, "Early Results of the Triage Medical Percutaneous Transfacet Pedicular BONE-LOK Compression Device for Lumbar Fusion", Accessed online Jul. 10, 2017, 10 pages.

Chiang, "Biomechanical Comparison of Instrumented Posterior Lumbar Interbody Fusion with One or Two Cages by Finite Element Analysis", Spine, Sep. 2006, pp. E682-E689, vol. 31(19), Lippincott Williams & Wilkins, Inc.

Brooks et al., "Efficacy of Supplemental Posterior Transfacet Pedicle Device Fixation in the Setting of One- or Two-Level Anterior Lumbar Interbody Fusion", Retrieved Jun. 19, 2017, 6 pages.

Brochure for PERPOS PLS System Surgical Technique by Interventional Spine, 2008, 8 pages.

Alfen et al., "Developments in the area of Endoscopic Spine Surgery", European Musculoskeletal Review 2006, pp. 23-24, Thessys(Trademark), Transforaminal Endoscopic Spine Systems, joi max Medical Solutions.

\* cited by examiner

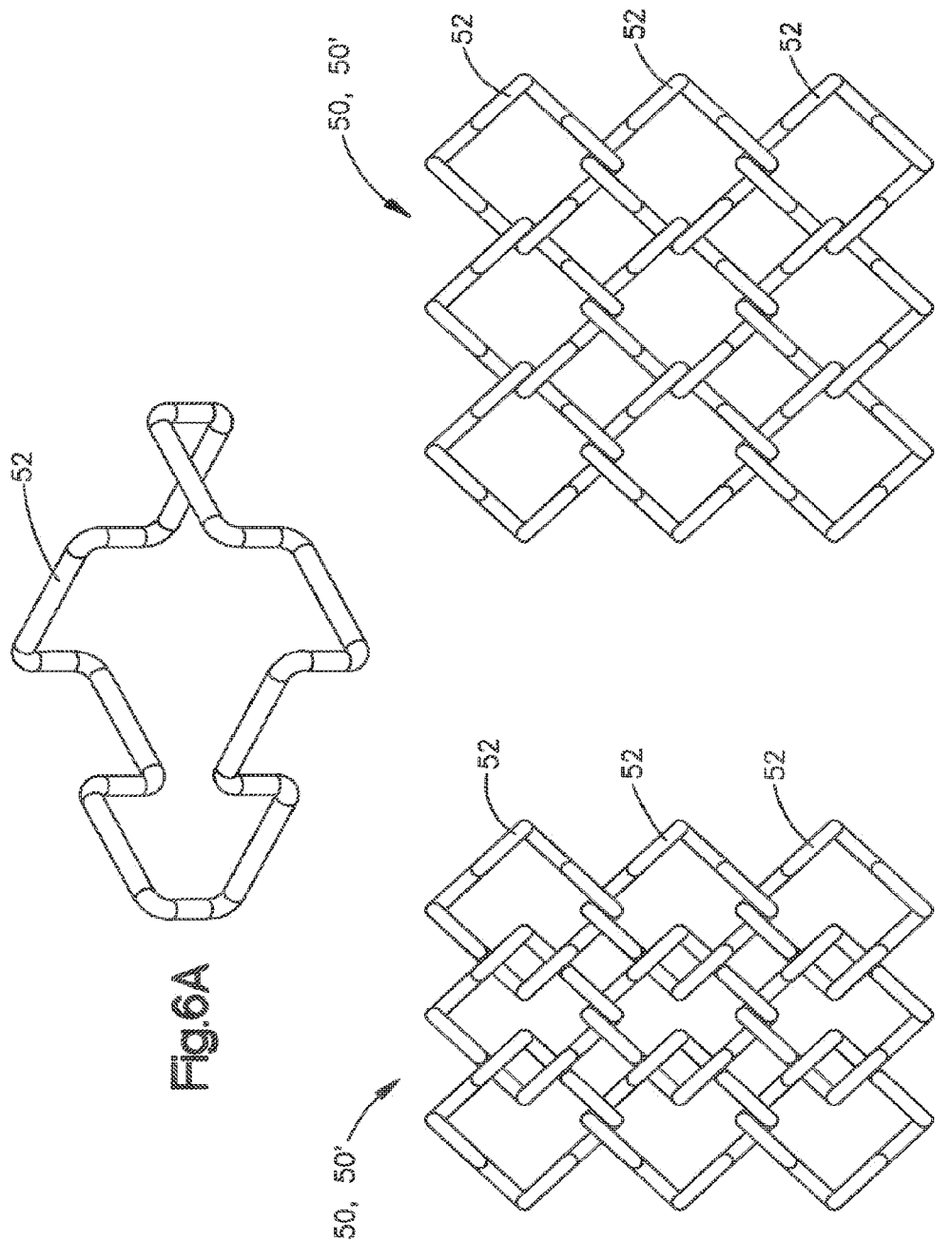

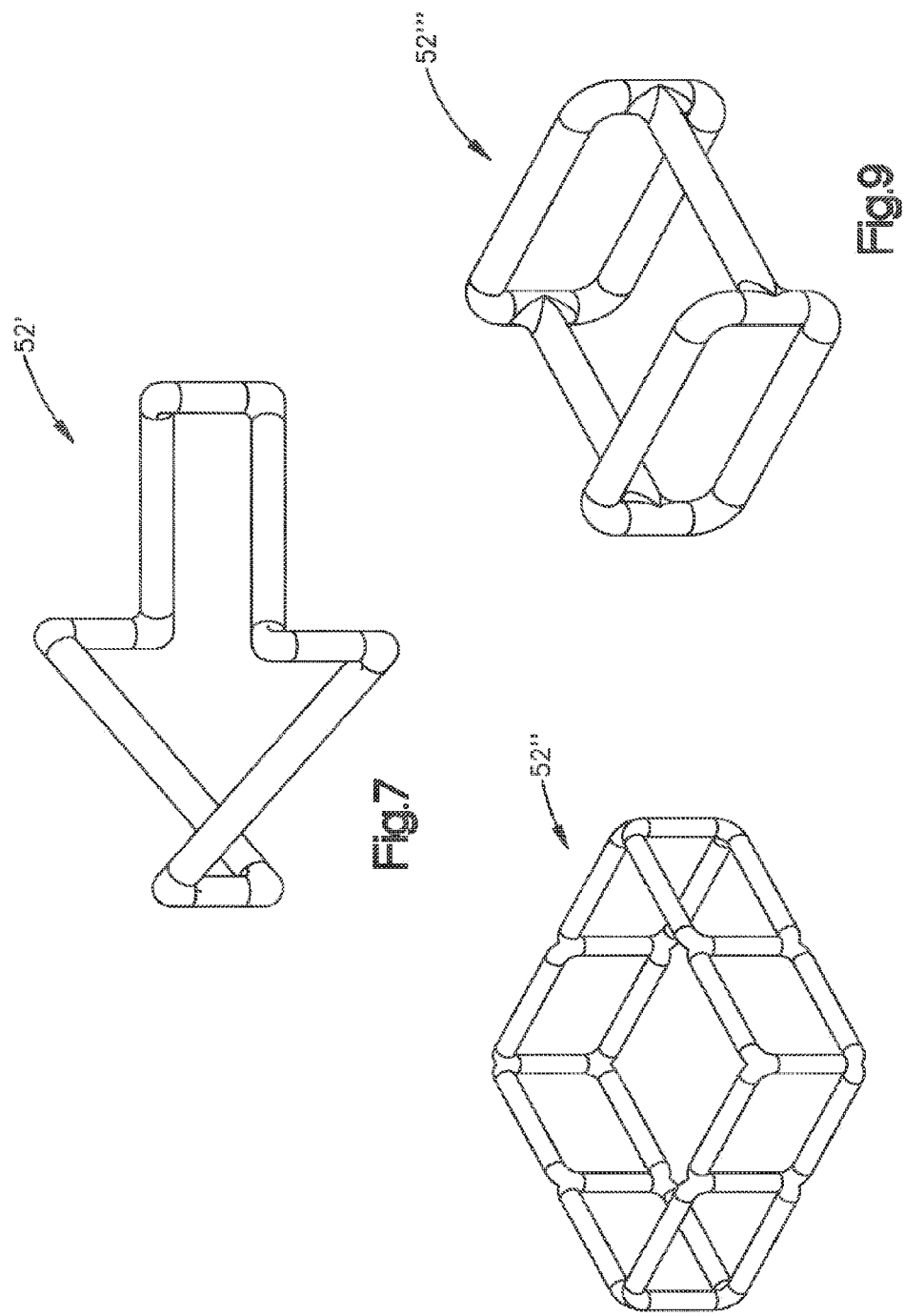

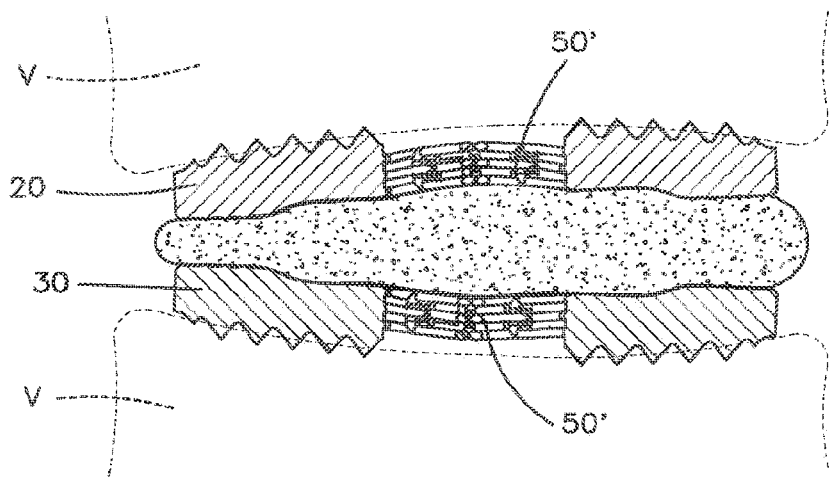
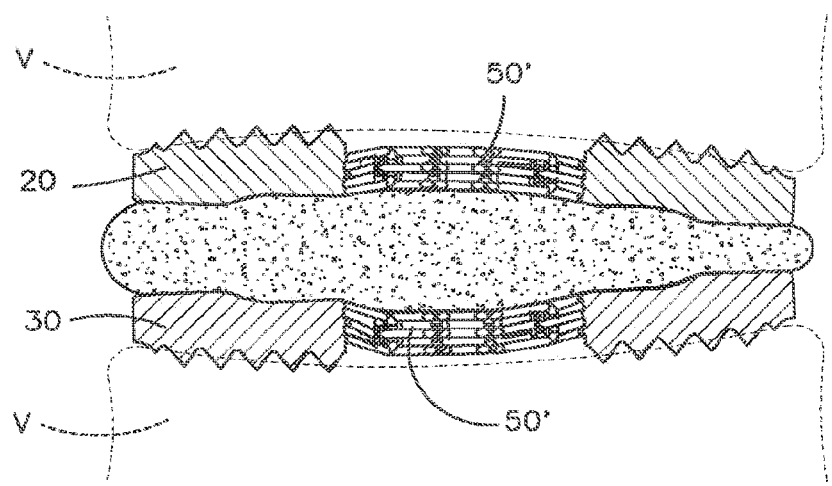
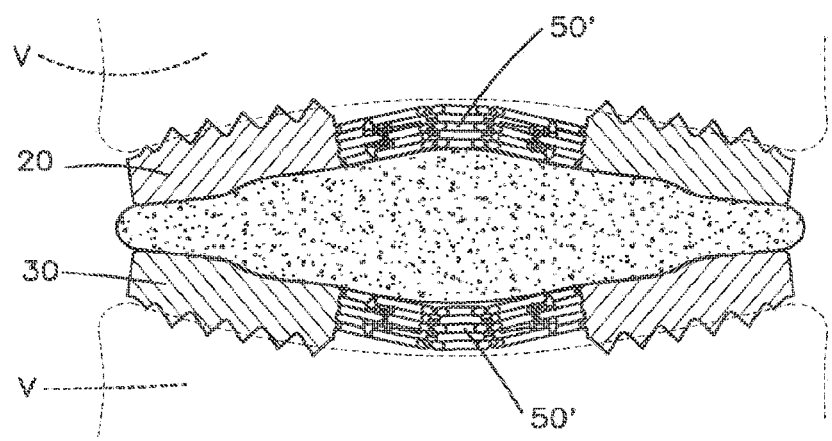

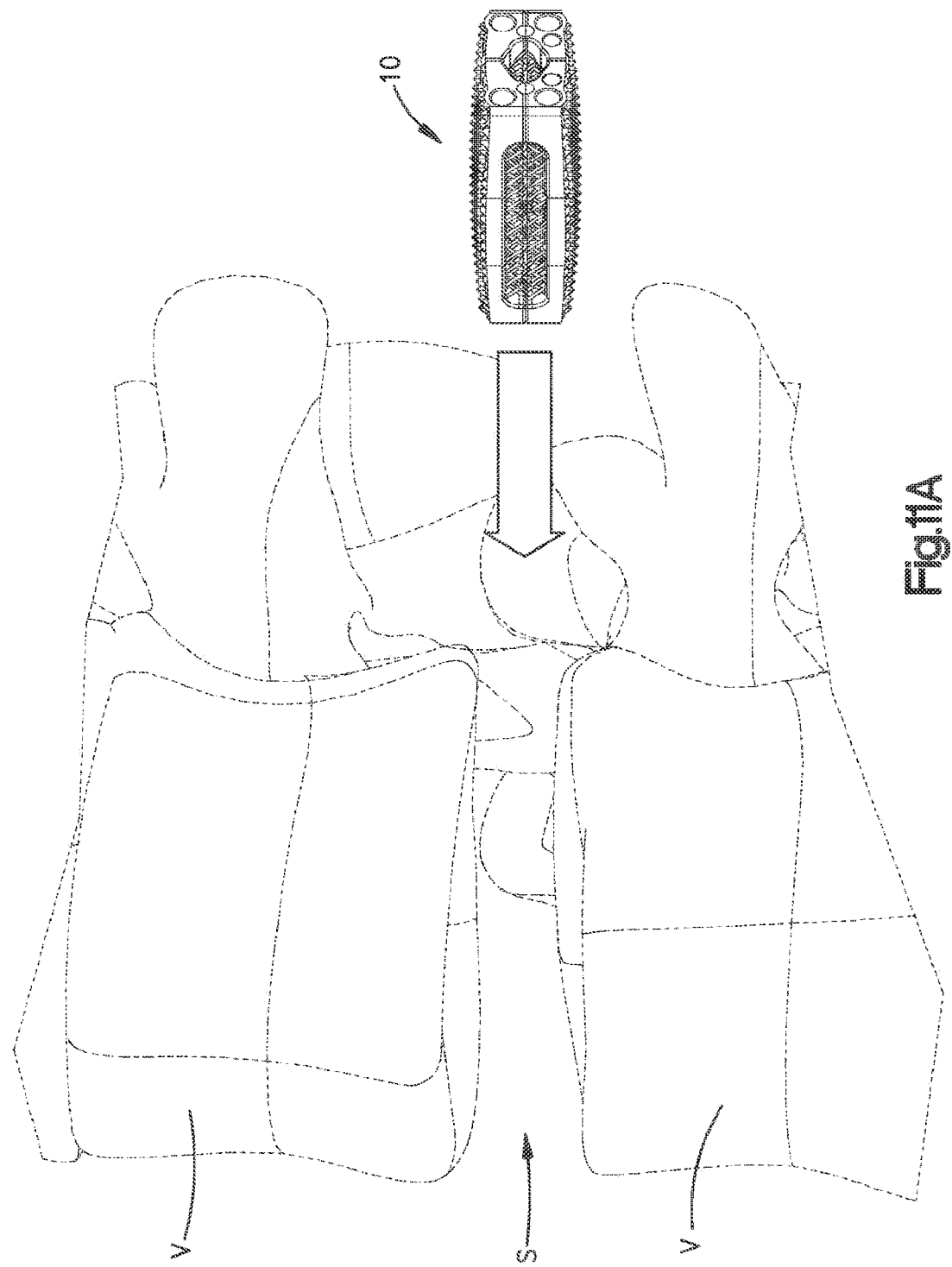

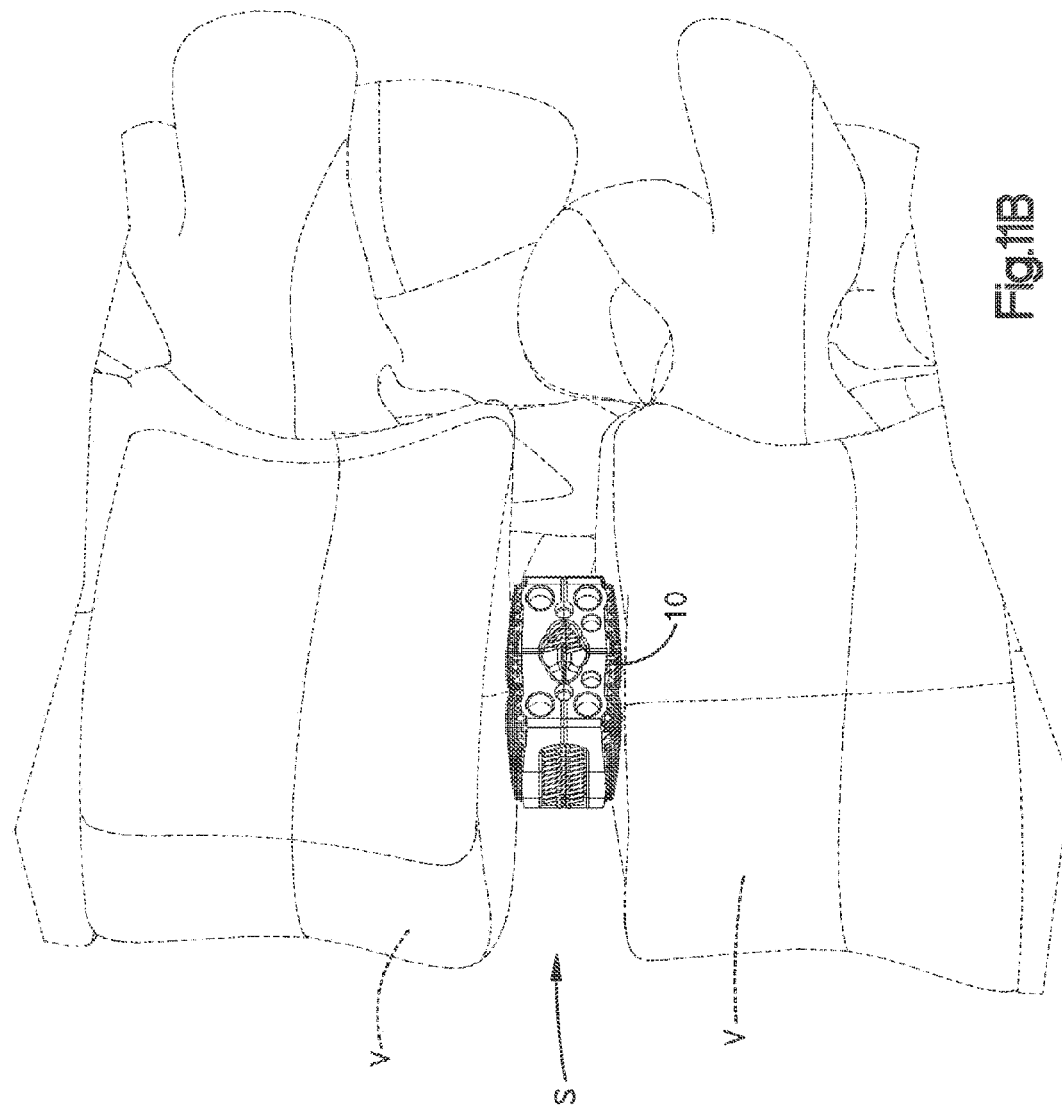

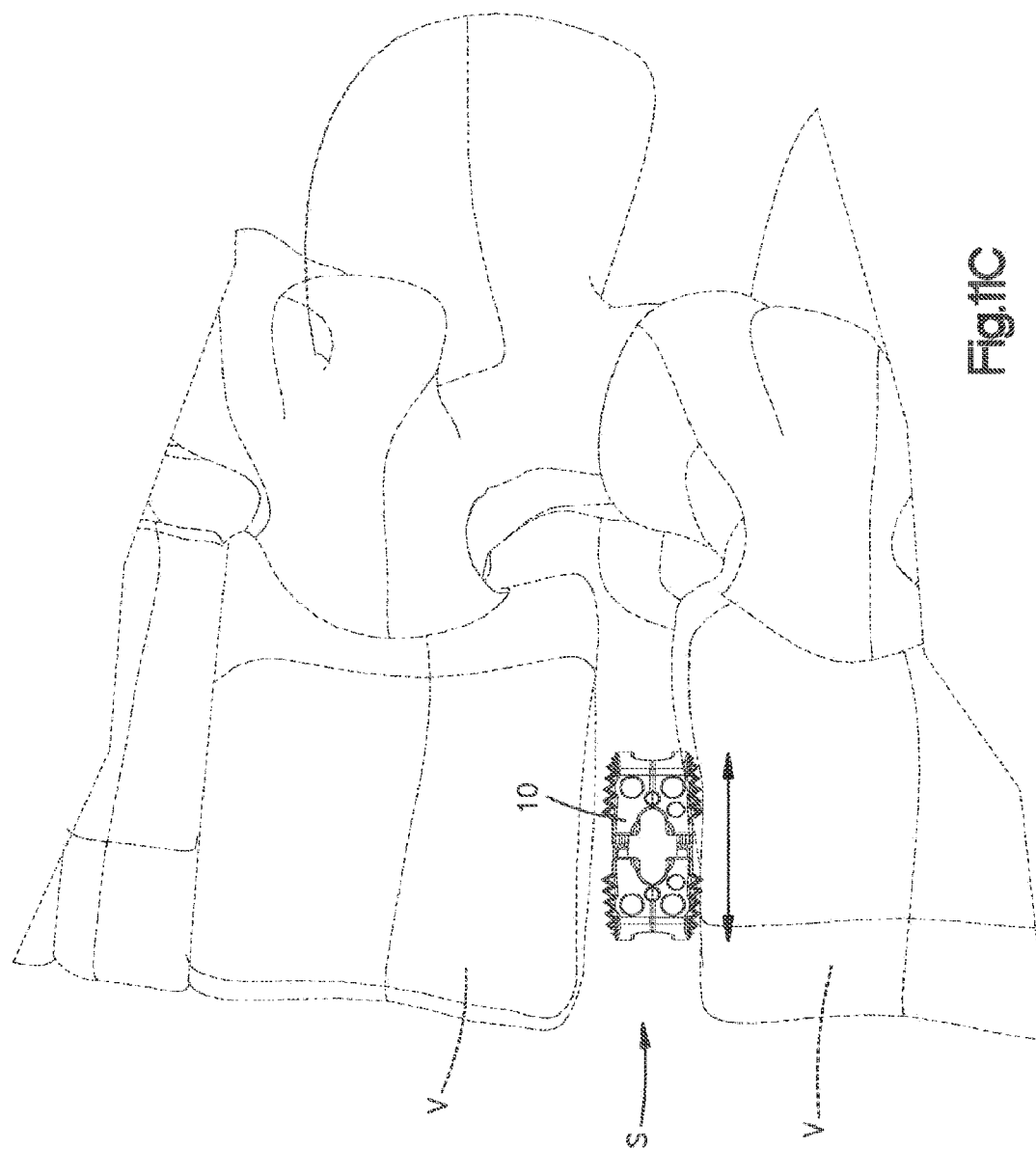

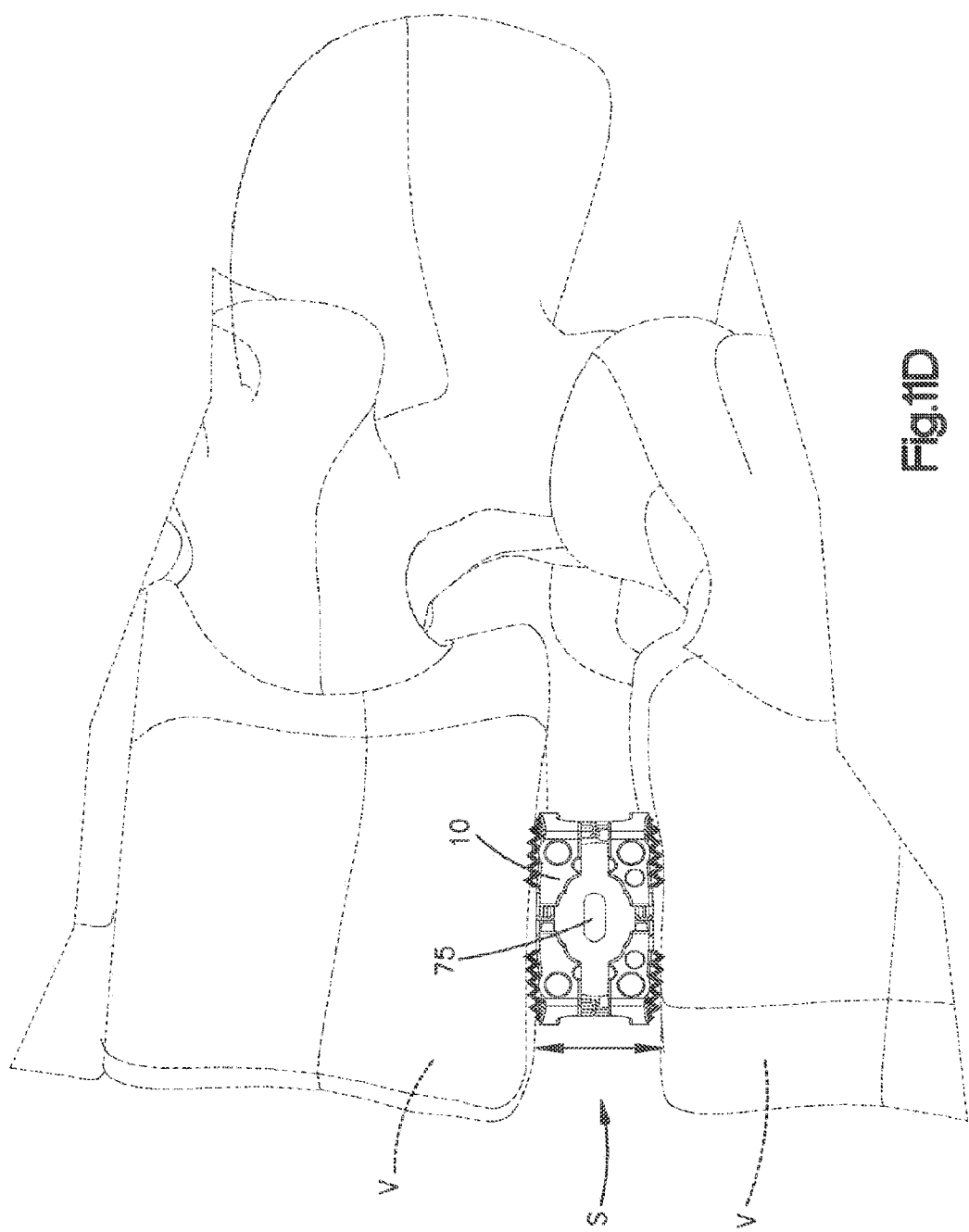

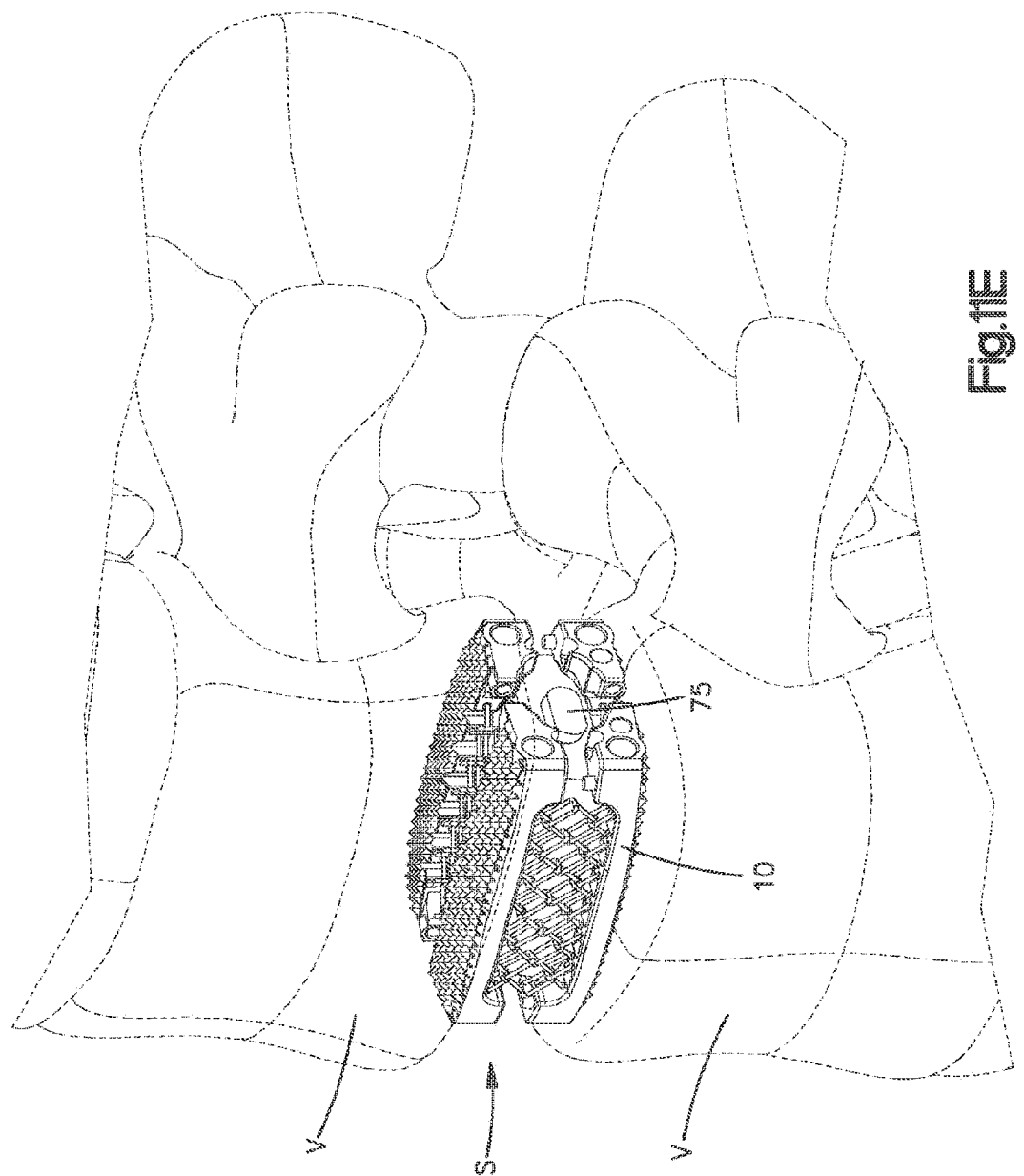

EXPANDABLE INTERVERTEBRAL IMPLANT AND ASSOCIATED METHOD OF MANUFACTURING THE SAME

CROSS REFERENCE TO RELATED APPLICATIONS

This application is a continuation of U.S. patent application Ser. No. 15/443,916 filed Feb. 27, 2017, which is a continuation of U.S. patent application Ser. No. 15/221,169 filed Jul. 27, 2016, now U.S. Pat. No. 9,597,197, which is a continuation of U.S. patent application Ser. No. 14/724,082, filed May 28, 2015, now U.S. Pat. No. 9,433,510, which is a continuation of U.S. patent application Ser. No. 14/032,231, filed Sep. 20, 2013, now U.S. Pat. No. 9,295,562, issued Mar. 29, 2016, which is a continuation of U.S. patent application Ser. No. 12/812,146, filed Jul. 8, 2010, now U.S. Pat. No. 8,551,173, issued Oct. 8, 2013, which is a national stage application under 35 U.S.C. § 371 of International Application No. PCT/US2009/031567, filed on Jan. 21, 2009, which claims the benefit of U.S. Provisional Application No. 61/021,778, filed on Jan. 17, 2008. The entire content of each aforementioned application is incorporated by reference herein for all purposes.

BACKGROUND

People, especially elderly people, may suffer from osteoporosis. One aspect of osteoporosis may be the partial or complete collapse of the bony structure of the spine, which in turn can cause loss of vertebral height, fracture of a vertebral disc, facet and nerve impingement, etc. Collapse of the spine often results in, for example, pain, reduction of lung function, unbalanced stature, etc. One treatment option may be a surgical procedure to re-align the vertebra (e.g., to re-establish balanced curvature of the spine as well as the intervertebral disc space).

Re-alignment of a spine including a damaged vertebra or disc may be accomplished by replacing the damaged vertebra, disc or portions thereof with an intervertebral implant. That is, an intervertebral implant may be inserted into the intervertebral disc space of two neighboring vertebral bodies or into the space created by removal of portions of or the entire vertebral body after removal of damaged portions of the spine. Preferably, the intervertebral implant restores the spine, as much as possible, to a natural state, i.e. to restore the original height of the intervertebral disc or the series of vertebra and, thus, the original distance between the two neighboring or adjacent vertebral bodies or vertebral bodies in various levels of the spine.

Typically implantation of one or more intervertebral implants is not part of a treatment procedure for osteoporosis. One reason for this may be that intervertebral implants are often designed with high structural stiffness. Osteoporotic bone is usually brittle, thus increasing the risk of breaking a vertebral endplate during a surgery or implantation of an implant and the endplates may have a uneven surface. For example, a stiff implant may impact a point or small area of an uneven surface of the osteoporotic bone, thereby creating a stress concentration and potentially damaging the bone. Therefore, the incorporation of an intervertebral implant in certain cases, is contra-indicated for patients with osteoporotic bone. Another reason for not incorporating an intervertebral implant may be that the insertion approach for implanting an intervertebral implant is difficult and risky, especially in elderly patients.

Alternatively, rather than implanting an intervertebral implant, a surgeon may elect to perform a Vertebralplasty and/or Cavitoplasty procedure on the patient's spine. In an exemplary method of performing a Vertebralplasty and/or Cavitoplasty procedure, a protective sleeve or cannula may be inserted into the patient's body, adjacent to the patient's spine. The spine may then be re-aligned if fractured or re-fractured. Next cement is inserted into the spine to replace lost bone and/or to limit future cracks. After the hardening of the cement, the treated section of the spine may be re-aligned and the patient may then return to his or her daily activity. In a Cavitoplasty procedure, a cavity may be formed in one or more of the vertebral bodies for receiving a portion of the cement.

It would be desirable to construct an intervertebral implant that is relatively simple to insert into a patient's spine at a relatively small size and which is able to expand to restore the original height of the removed spinal material or to a height desired by a surgeon. It would also be desirable to construct an intervertebral implant that is adaptable to uneven surfaces of an osteoporotic vertebral bone to limit stress concentrations when the implant is expanded and contacts or applies pressure to a patient's endplate.

SUMMARY

The present invention relates to an expandable intervertebral implant. More particularly, a preferred embodiment of the present invention relates to an intervertebral implant that is laterally and vertically expandable in situ from a collapsed, non-expanded or first insertion configuration to a second expanded configuration. The expandable intervertebral implant preferably includes superior and inferior bone contacting members connected together via one or more expandable components such as, for example, a wire netting so that the implant is vertically expandable in the cranio/caudal direction. The superior and inferior bone contacting members preferably are formed by two or more bone contacting components connected together via one or more expandable components such as, for example, a wire netting so that the implant is laterally expandable in the lateral direction if implanted via an anterior approach or laterally expandable in the anterior-posterior direction if implanted via a lateral approach.

The present invention also relates to an associated method of inserting and sequentially expanding the intervertebral implant and an associated method of manufacturing the intervertebral implant such that the intervertebral implant can be manufactured as an integral component.

BRIEF DESCRIPTION OF THE DRAWINGS

The foregoing summary, as well as the following detailed description of the preferred embodiments of the application, will be better understood when read in conjunction with the appended drawings. For the purposes of illustrating the expandable intervertebral implant, surgical method for implanting the intervertebral implant and manufacturing method for forming the intervertebral implant of the present application, there are shown in the drawings preferred embodiments. It should be understood, however, that the application is not limited to the precise arrangements and instrumentalities shown. In the drawings:

FIG. 6A illustrates a top perspective view of a first preferred embodiment of a link member that may be used to form wire netting that may be used in conjunction with the intervertebral implant shown in FIG. 1;

FIG. 6B illustrates a top plan view of the wire netting shown in FIG. 6A, the wire netting illustrated in an at least partially collapsed, non-expanded or first insertion configuration;

FIG. 6C illustrates a top plan view of the wire netting shown in FIG. 6A, the wire netting illustrated in the second expanded configuration;

FIG. 7 illustrates a top perspective view of a second preferred embodiment of a link member that may be used to form wire netting that may be used in conjunction with the intervertebral implant shown in FIG. 1;

FIG. 8 illustrates a top perspective view of a third preferred embodiment of a link member that may be used to form wire netting that may be used in conjunction with the intervertebral implant shown in FIG. 1;

FIG. 9 illustrates a top perspective view of a fourth preferred embodiment of a link member that may be used to form wire netting that may be used in conjunction with the intervertebral implant shown in FIG. 1;

FIGS. 10A-10C illustrate various cross-sectional views of the intervertebral implant shown in FIG. 1, the superior and inferior bone contacting members incorporating wire netting so that the superior and inferior bone contacting members are able to adapt and/or conform to the endplates of the superior and inferior vertebral bodies V, respectively;

FIGS. 11A-11E illustrate various perspective views of steps of an exemplary surgical method for laterally inserting the expandable intervertebral implant of FIG. 1 in accordance with one aspect of the preferred invention.

DETAILED DESCRIPTION OF ILLUSTRATIVE EMBODIMENTS

Figure 1:
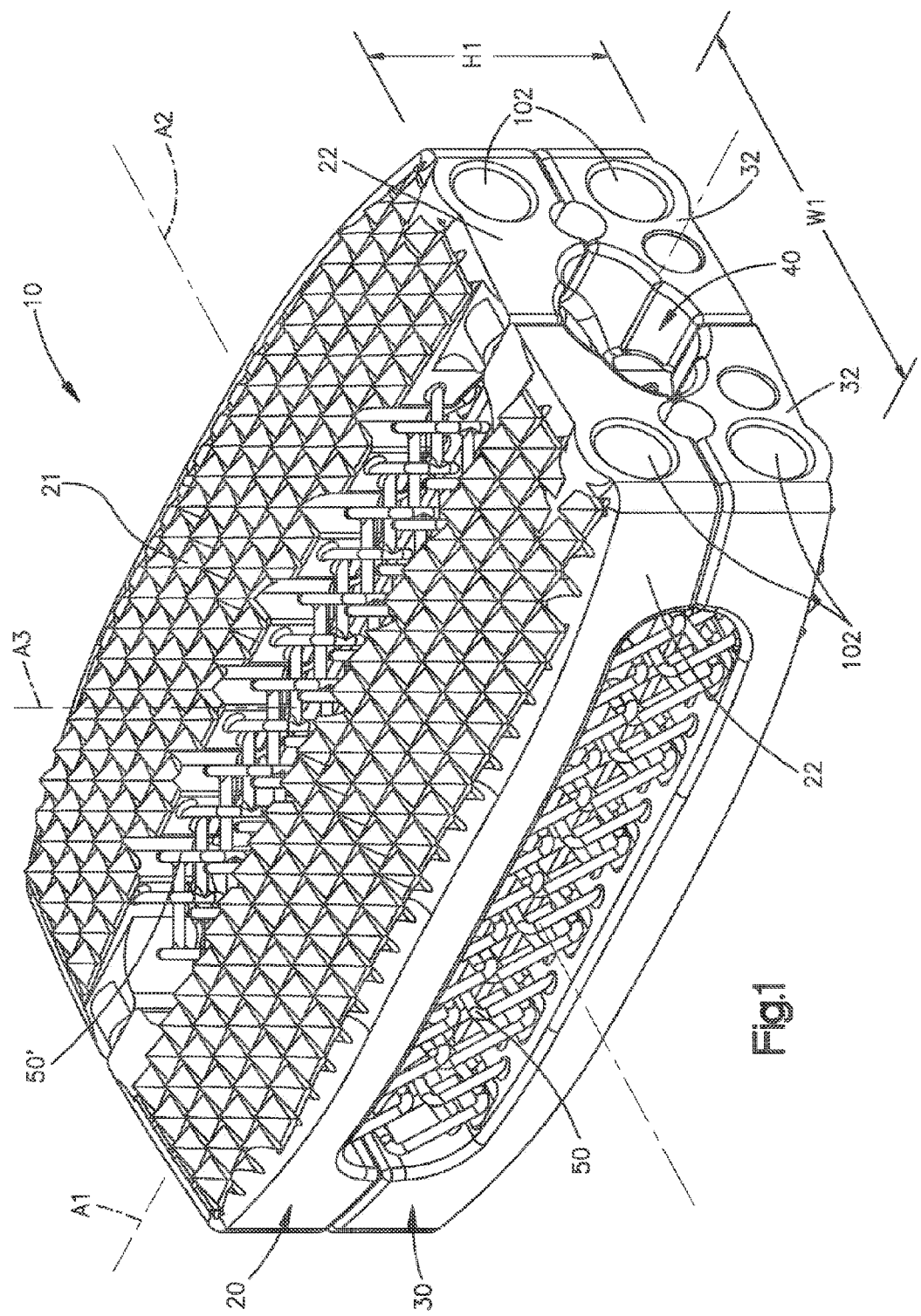
FIG. 1 illustrates a top perspective view of an exemplary intervertebral implant according to the present invention, the implant illustrated in the collapsed, non-expanded or first insertion configuration

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior", "lateral" and related words and/or phrases designate preferred positions and orientations in the human body to which reference is made and are not meant to be limiting. The terminology includes the above-listed words, derivatives thereof and words of similar import.

Certain exemplary embodiments of the invention will now be described with reference to the drawings. In general preferred embodiments of the present invention are directed to (i) an expandable intervertebral implant 10 for implantation between or to replace damaged portions of adjacent vertebral bodies V in a patient's spine (for example, in the lumbar, thoracic or cervical regions), (ii) an exemplary surgical method for implanting the intervertebral implant 10 between adjacent vertebral bodies V in the patient's spine and (iii) an exemplary method of manufacturing the intervertebral implant 10. More specifically, the present invention is preferably directed to an expandable intervertebral implant 10 for total or partial disc or vertebral body V replacement or for nucleus replacement of an intervertebral disc space S. It should be appreciated that while the expandable intervertebral implant 10 of the present application will be described in connection with spinal disc replacement, one of ordinary skill in the art will understand that the implant 10 as well as the components thereof may be used for replacement of tissue in other parts of the body including, for example, knee, hip, shoulder, finger or other joint replacement or for bone augmentation.

Figure 2:
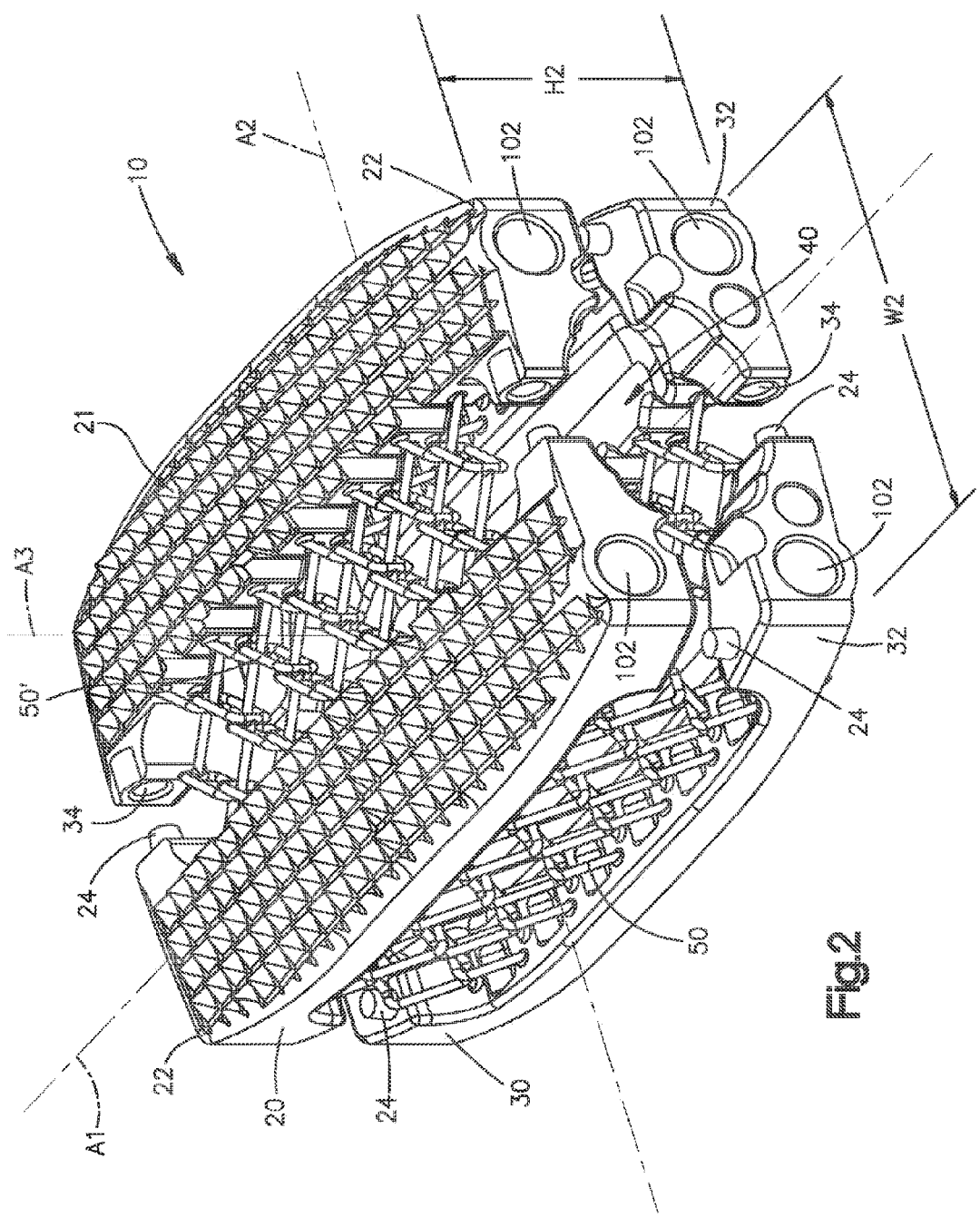
FIG. 2 illustrates a top perspective view of the intervertebral implant shown in FIG. 1, the implant illustrated in a second, expanded configuration.
Figure 3A:
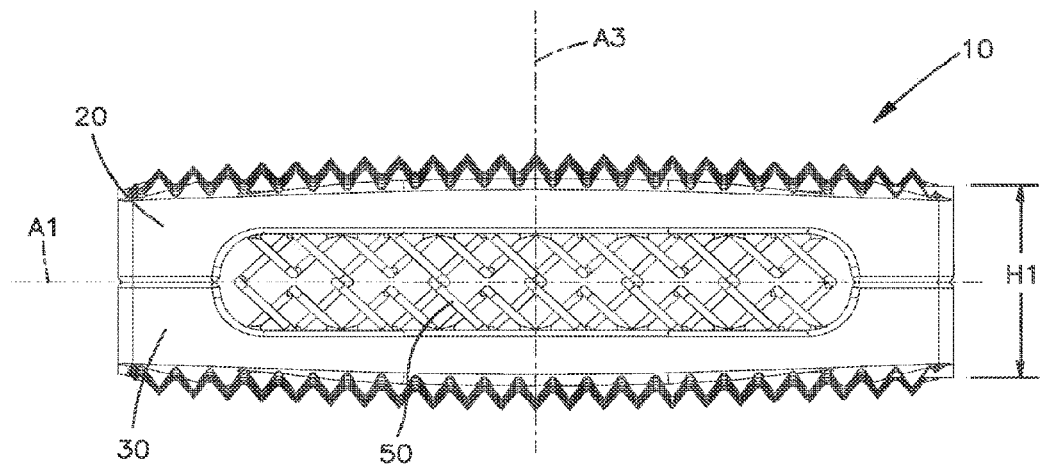
FIG. 3A illustrates a side elevational view of the intervertebral implant shown in FIG. 1, the implant illustrated in the collapsed, non-expanded or first insertion configuration.
Figure 3B:
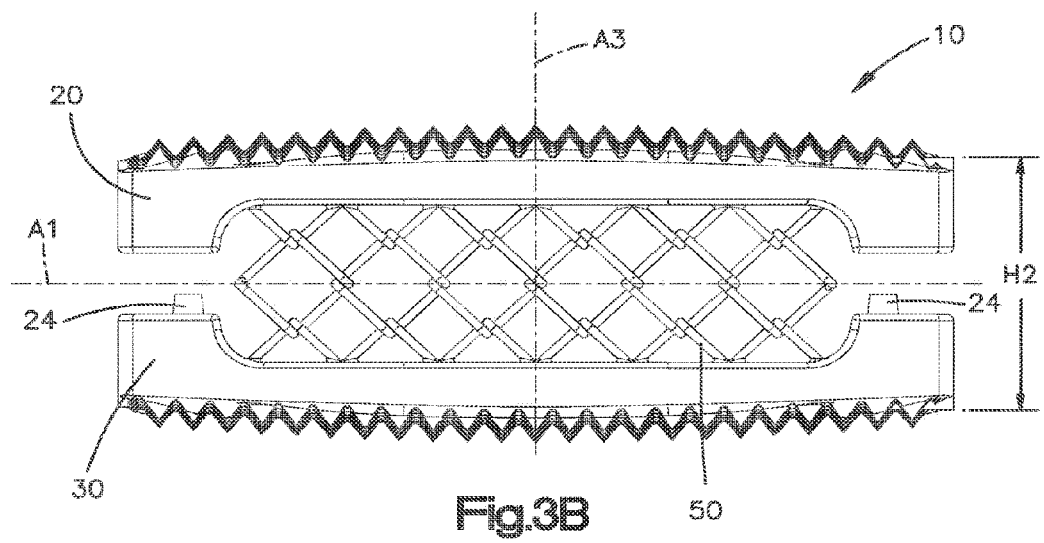
FIG. 3B illustrates a side elevational view of the intervertebral implant shown in FIG. 1, the implant illustrated in the second expanded configuration.
Figure 4A:
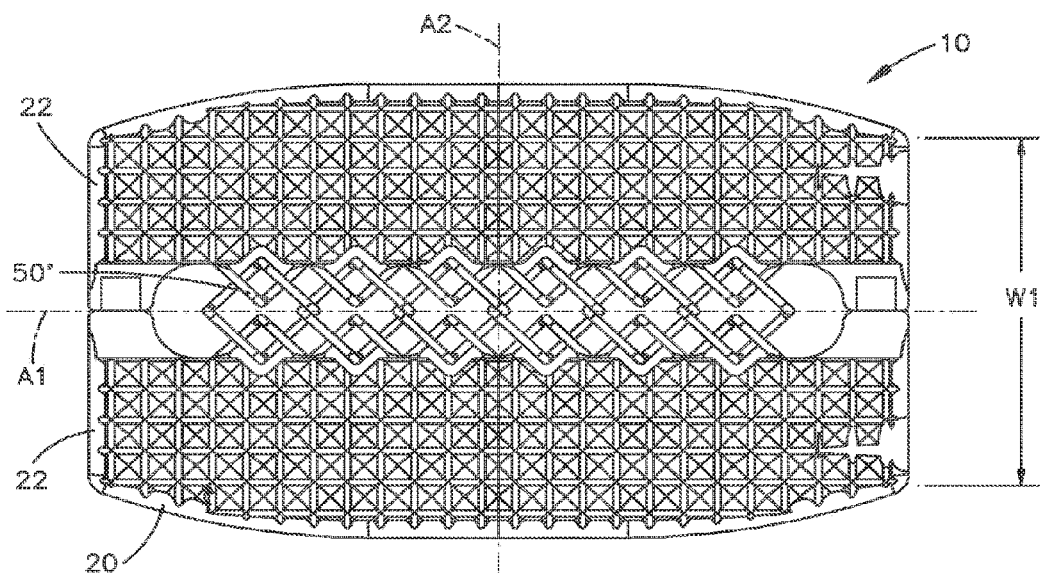
FIG. 4A illustrates a top plan view of the intervertebral implant shown in FIG. 1, the implant illustrated in the collapsed, non-expanded or first insertion configuration.
Figure 4B:
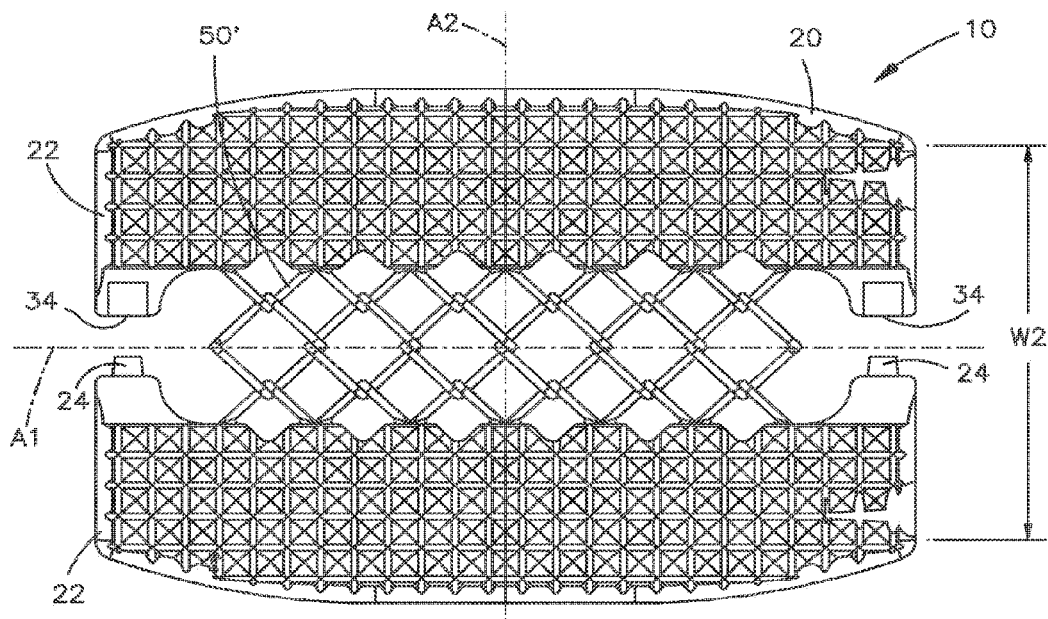
FIG. 4B illustrates a top plan view of the intervertebral implant shown in FIG. 1, the implant illustrated in the second expanded configuration.
Figure 5A:
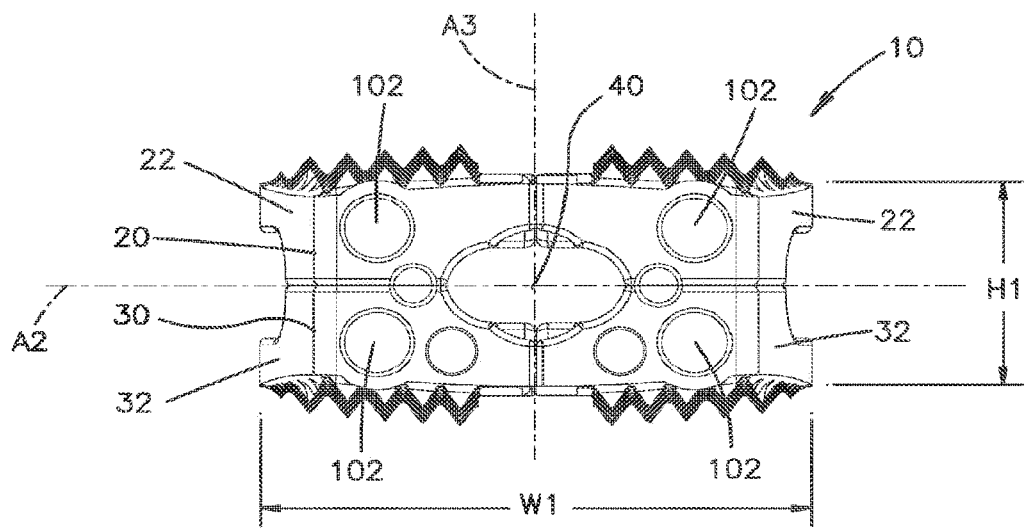
FIG. 5A illustrates a front elevational view of the intervertebral implant shown in FIG. 1, the implant illustrated in the collapsed, non-expanded or first insertion configuration.
Figure 5B:
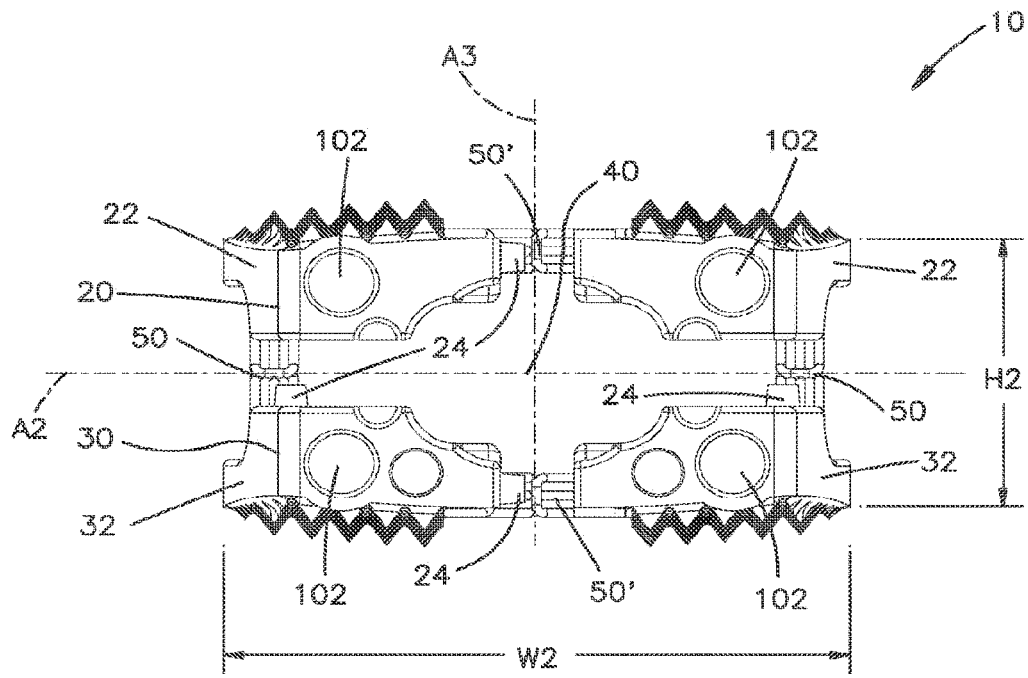
FIG. 5B illustrates a front elevational view of the intervertebral implant shown in FIG. 1, the implant illustrated in the second expanded configuration.

Referring to FIGS. 1-5B, as will be described in greater detail below, the expandable intervertebral implant 10 is preferably used for intervertebral support of the spine for patients that require interbody fusion at one or more levels of the spine. The expandable intervertebral implant 10 is preferably implanted by a surgeon into the patient's body in a collapsed, non-expanded or first insertion configuration (as best shown in FIGS. 1, 3A, 4A and 5A), thereby allowing a smaller incision than is typically necessary for implantation of a non-expandable intervertebral implant (not shown). Implantation of the preferred expandable intervertebral implant 10 in the first insertion configuration may also make it easier to insert the implant 10 past structures that may inhibit a surgeon's access to the spine. The expandable intervertebral implant 10 allows surgeons to implant a larger intervertebral implant in the disc space S, generally without having to do an excessive amount of boney resection and soft tissue retraction. Once the implant 10 is inserted into the disc space S, the implant 10 may be expanded to a second expanded configuration (as best shown in FIGS. 2, 3B, 4B and 5B). More preferably, the implant 10 is expandable in the cranio/caudal direction to provide parallel and/or lordotic intervertebral distraction and in the lateral direction. That is, the expandable intervertebral implant 10 is preferably implanted by a surgeon into the patient's body in a collapsed, non-expanded or first insertion configuration wherein the implant has a first height $H_1$ and a first width $W_1$. Thereafter, once inserted into the disc space S, the implant 10 may be expanded to a second expanded configuration wherein the implant 10 has a second height $H_2$ and a second width $W_2$, wherein the second height $H_2$ and the second width $W_2$ are larger than the first height $H_1$ and the first width $W_1$, respectively.

The preferred expandable intervertebral implant 10 may, for example, fill the entire intervertebral disc space S to replace the entire intervertebral disc. Alternatively, a plurality of expandable intervertebral implants 10 may be used to fill the intervertebral disc space S. For example, two or more smaller expandable intervertebral implants 10 may be used to fill the intervertebral disc space S. Alternatively, the expandable intervertebral implant 10 may be sized and configured to only partially replace an intervertebral disc space S, such as for example, to replace a nucleus. In addition, the preferred intervertebral implant 10 may be configured to replace a disc and a portion of a damages vertebra V.

The expandable intervertebral implant 10 preferably includes a superior bone contacting member 20 for contacting a first, superior vertebra V, an inferior bone contacting member 30 for contacting a second, inferior vertebra V and a vertical wire netting or mesh 50 for interconnecting the superior and inferior bone contacting members 20, 30 with respect to one another. The vertical wire netting 50 preferably enables the superior and inferior bone contacting members 20, 30 to move (e.g., expand) in the cranial/caudal direction or generally away from each other during movement from the collapsed, non-expanded or first insertion configuration to the second expanded configuration when the implant 10 is inserted into the disc space S. The superior and inferior bone contacting members 20, 30 are sized and configured to contact at least a portion of the endplates of the superior and inferior vertebral bodies V, respectively, or to engage a surface of the superior and/or inferior vertebral bodies V remaining after damaged portions of the superior and/or inferior vertebrae V are removed from the spine. The superior and inferior bone contacting members 20, 30 preferably define a cavity 40 therebetween.

The superior bone contacting member 20 of the exemplary preferred embodiment is formed by two or more bone contacting components 22 interconnected by a lateral wire netting or mesh 50'. Similarly, the inferior bone contacting member 30 of the exemplary preferred embodiment is formed by two or more bone contacting components 32 interconnected by the lateral wire netting 50'. That is, the superior and inferior bone contacting members 20, 30 are each preferably constructed by a plurality of generally rigid bone contacting components 22, 32 separated by or interconnected by the lateral expandable wire netting 50' so that the bone contacting components 22, 32, which form the bone contacting members 20, 30, are moveable (e.g., expandable) with respect to one another. As shown, the bone contacting components 22, 32 preferably are in the form of one or more plates, more preferably an L-shaped plate, although other shapes are contemplated. However, the bone contacting members 20, 30 may be constructed as a single integral component, for example, if the implant 10 is constructed to expand only in the cranial/caudal direction. In addition, the superior and inferior bone contacting members 20, 30 may have convex-shaped surfaces wherein they contact the endplates of the vertebra V to conform to the shape of the endplates.

In this manner, by incorporating the vertical wire netting 50 between the superior and inferior bone contacting members 20, 30, the implant 10 is expandable from the collapsed, non-expanded or first insertion configuration wherein the implant 10 has a first height $H_1$ to the second expanded configuration wherein the implant 10 has a second height $H_2$, wherein the second height $H_2$ is larger than the first height $H_1$. Similarly, by incorporating the lateral wire netting 50' between the adjacent bone contacting components 22, 32, which form the superior and inferior bone contacting members 20, 30, respectively, the implant 10 is expandable from the collapsed, non-expanded or first insertion configuration wherein the implant 10 has a first width $W_1$ to a second expanded configuration wherein the implant 10 has a second width $W_2$, wherein the second width $W_2$ is larger than the first width $W_1$. That is, the lateral wire netting 50' preferably enables the bone contacting components 22, 32 to be laterally moveable (e.g., in the anterior-posterior or lateral direction depending on insertion procedure) with respect to one another along a lateral axis A2 while the vertical wire netting 50 enables the superior and inferior bone contacting members 20, 30 to be vertically moveable with respect to one another along a vertical axis A3. In addition, the vertical and lateral wire netting 50, 50' enables the superior bone contacting member 20 to move with respect to the inferior bone contacting member 30 along a longitudinal axis A1. Thus, the vertical and lateral wire netting 50, 50' enables the implant 10 to conform its final shape in the second or expanded configuration to mate to the typically uneven surfaces of the endplates of the vertebral bodies V. In addition, the vertical and lateral wire netting 50, 50' enables the implant 10 to limit stress risers at contact points between the implant 10 and the vertebral bodies V thus making the preferred implant 10 applicable for insertion between osteoporotic bone.

That is, in the preferred embodiment, by forming the preferred implant 10 from four bone contacting components 22, 32 interconnected by vertical and lateral wire netting 50, 50', the superior and inferior bone contacting members 20, 30 of the implant 10 are preferably able to move in six degrees of freedom with respect to each other. Specifically, the superior and inferior bone contacting members 20, 30 are able to move longitudinally relative to each other along the longitudinal axis A1, laterally relative to each other along the lateral axis A2, vertically relative to each other along the vertical axis A3, pivot or roll relative to each other about the longitudinal axis A1, pivot or pitch relative to each other about the lateral axis A2 and pivot or yaw relative to each other about the vertical axis A3. Accordingly, the preferred implant 10 is able to conform its final shape in the second or expanded configuration to mate to the typically uneven surfaces of the endplates of the vertebral bodies V and limit stress risers at contact points between the implant 10 and the vertebral bodies V.

It should be noted that it is also envisioned that the superior and inferior bone contacting members 20, 30 may be formed of four or more bone contacting components 22, 32 interconnected by lateral wire netting 50' and longitudinal wire netting (not shown) so that the implant 10 is longitudinally moveable from a first length to a second length (not shown). Alternatively, the superior and inferior bone contacting members 20, may be formed of two bone contacting components 22, 32 interconnected by longitudinal wire netting (not shown) but not lateral wire netting 50' so that the implant 10 is longitudinally moveable from a first length to a second length (not shown) but not laterally moveable from the first width $W_1$ to the second width $W_2$.

Figure 12A:
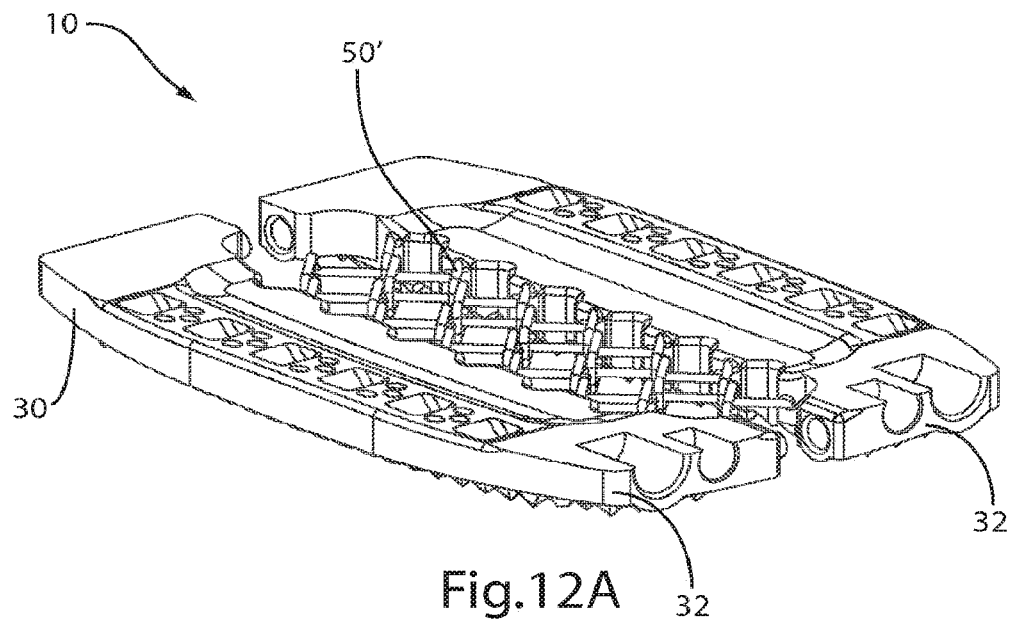
FIGS. 12A-12L illustrate various top, perspective views of steps of an exemplary method for manufacturing the expandable intervertebral implant of FIG. 1 in accordance with one aspect of the preferred invention.
Figure 12B:
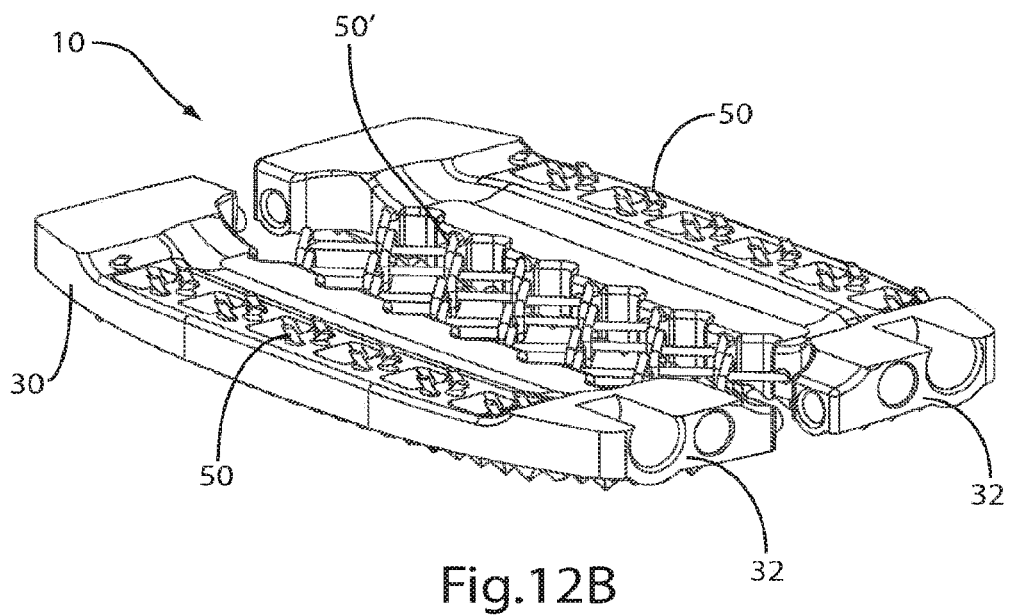
Figure 12C:
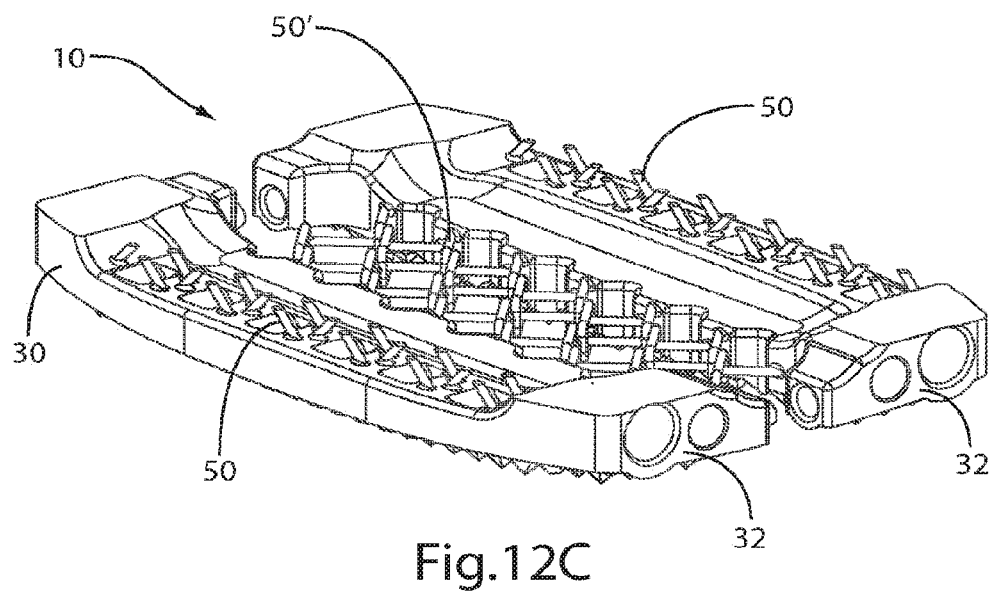
Figure 12D:
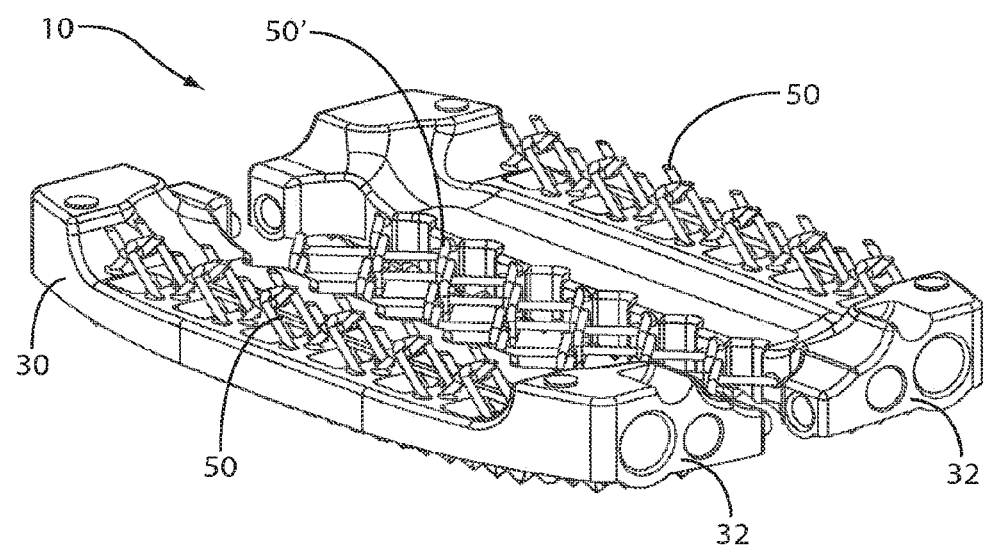
Figure 12E:
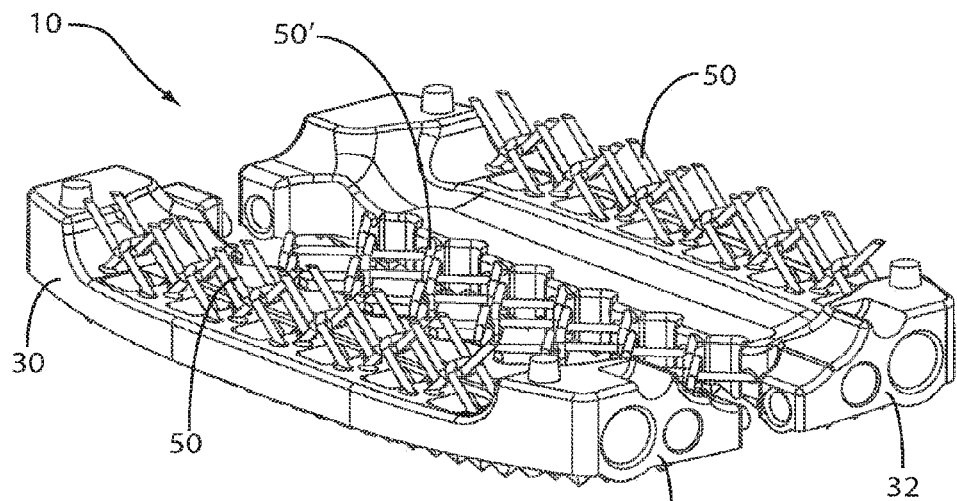
Figure 12F:
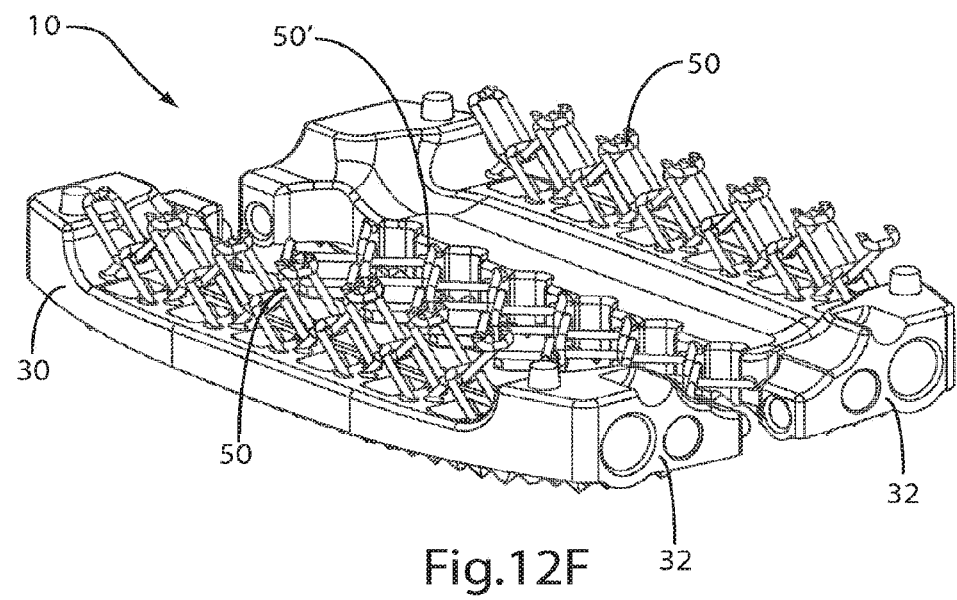
Figure 12G:
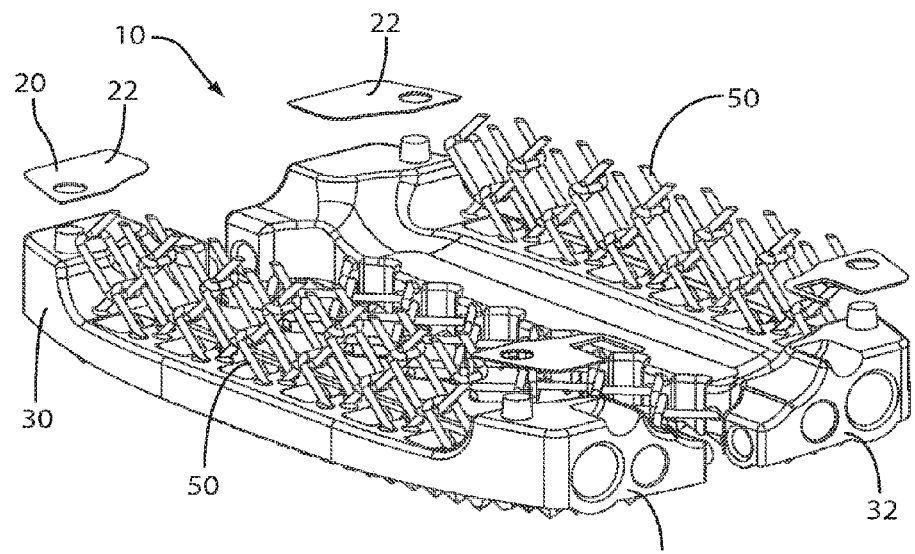
Figure 12H:
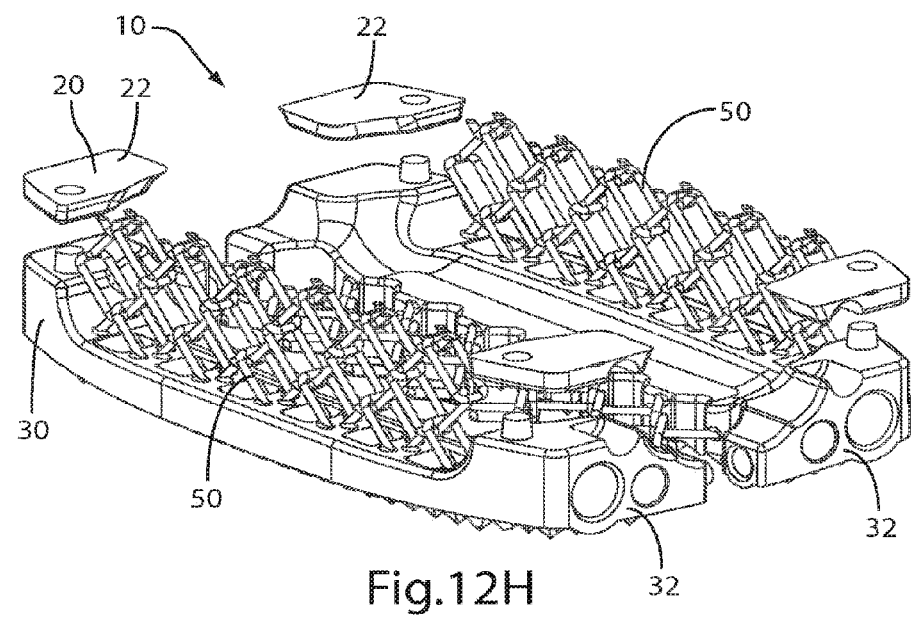
Figure 12I:
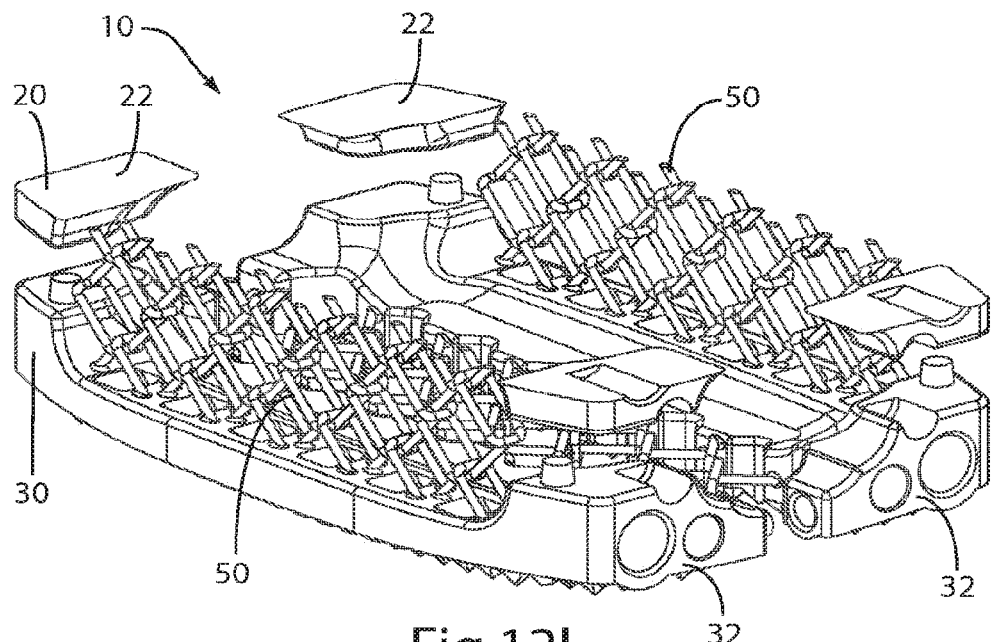
Figure 12J:
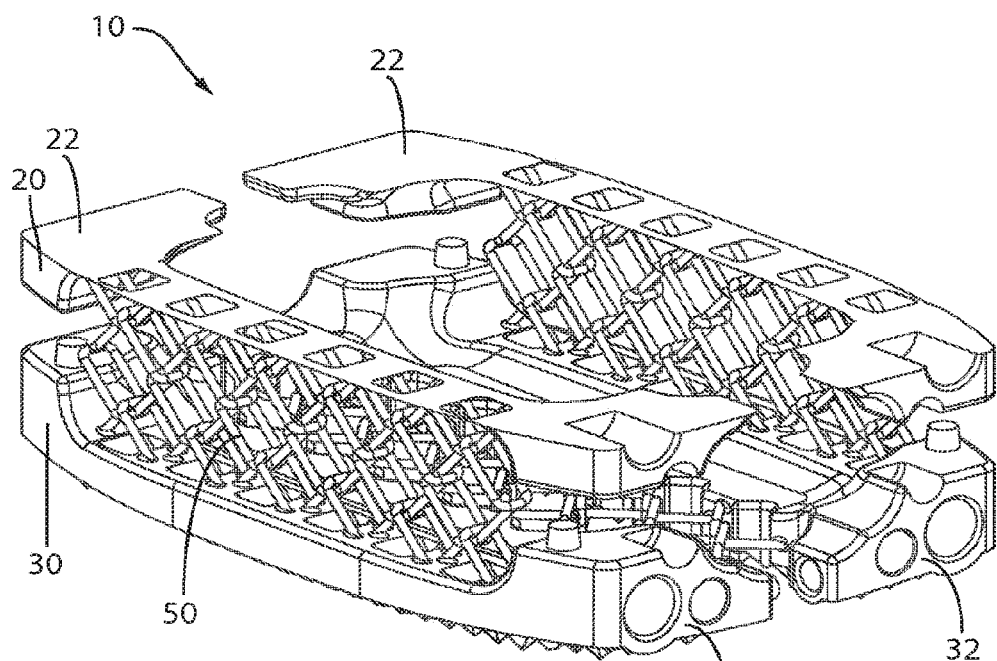
Figure 12K:
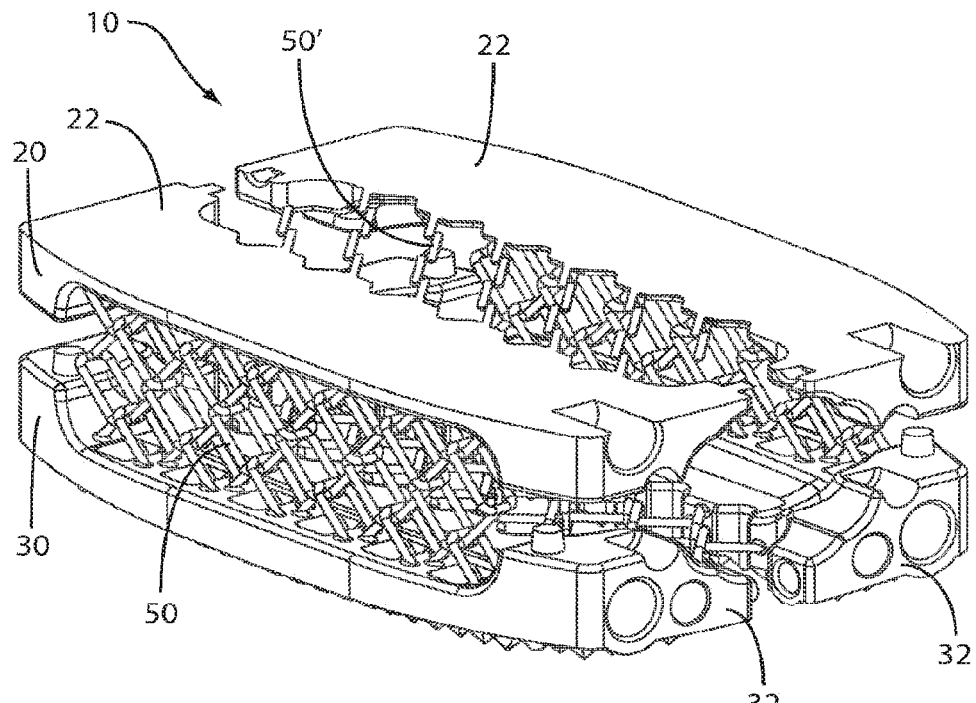
Figure 12L:
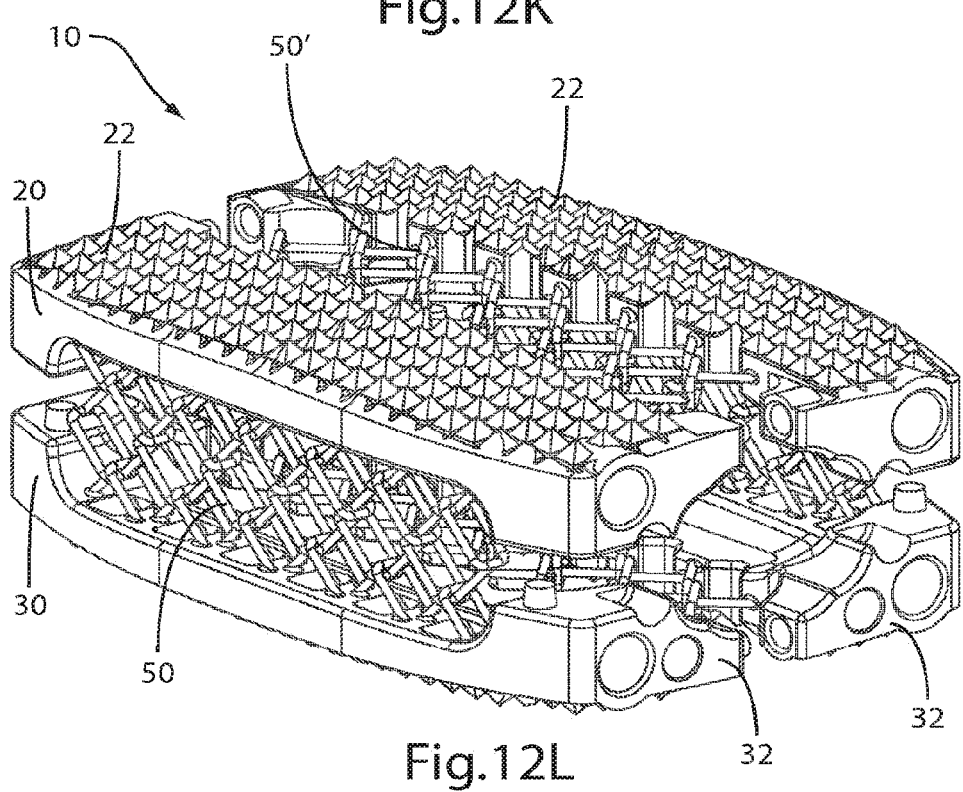

The vertical wire netting 50 and the lateral wire netting 50', preferably enable approximately three tenths of a millimeter (0.3 mm) to approximately twelve millimeters (12 mm) of movement, although other amounts of movement are permissible as would be apparent to one having ordinary skill in the art. Further, the implant is not limited to having the generally rectangular or box-shaped configuration shown in FIGS. 1-12L, for example, the implant 10 may have a generally circular or cylindrical-shaped series of rings that form the superior and inferior bone contacting members 20, 30 separated by wire netting such that an inner ring may expand along the vertical axis A3 further than an outer ring to conform to a concave-shaped endplate.

Referring to FIGS. 6A-6C, a first preferred, exemplary embodiment of the vertical and/or lateral wire netting 50, 50' is formed by interconnecting a plurality of individual first link members 52. As shown, the plurality of individual first link members 52 may have a generally rectangular shape when at least partially expanded but are not so limited. Referring to FIG. 7, a second preferred exemplary embodiment of the lateral and/or vertical wire netting 50, 50' may be formed by interconnecting a plurality of individual second link members 52' wherein the plurality of individual second link members 52' have a generally trapezoidal shape when at least partially expanded but are not so limited. Referring to FIG. 8, a third preferred, exemplary embodiment of the vertical and/or lateral wire netting 50, 50' may be formed by interconnecting a plurality of individual third link members 52" wherein the plurality of individual think link members 52" have an alternate, second rectangular shape when at least partially expanded but are not so limited. Referring to FIG. 9, a fourth preferred, exemplary embodiment of the vertical and/or lateral wire netting 50, 50' may be formed by interconnecting a plurality of individual fourth link members 52''' wherein the plurality of individual fourth link members 52''' have an alternate, third rectangular shape when at least partially expanded but are not so limited. Alternatively, the vertical and/or lateral wire netting 50, 50' may have any other form or shape such as, for example, a plastically deformable material, mesh, stent, etc. so long as the vertical and/or lateral wire netting 50, 50' interconnects and enables the superior and inferior bone contacting members 20, and/or the superior and inferior bone contacting components 22, 32 to move with respect to one another. The preferred individual link members 52, 52', 52", 52''' are not limited to the generally rectangular or trapezoidal shapes and may take nearly any shape such as, for example, oval, circular, triangular, hexagonal, etc.

In addition, by forming or constructing the vertical and/or lateral wire-netting 50, 50' from a plurality of preferred individual first, second, third and/or fourth link members 52, 52', 52", 52''' the superior and/or inferior bone contacting components 22, 32 are able to tilt or generally move with respect to one another so that the superior and inferior bone contacting members 20, 30 are better able to conform to the configuration of the endplates of the adjacent vertebral bodies V. That is, as previously described above, by forming the preferred implant 10 from four bone contacting components 22, 32 interconnected by vertical and lateral wire netting 50, 50', the flexible of the vertical and/or lateral wire netting 50, 50' enables the superior and inferior bone contacting members 20, 30 of the implant 10 to move in six degrees of freedom with respect to each other so that the implant 10 and more particularly the superior and inferior bone contacting members 20, 30 are better able to adapt and/or conform to the anatomical shape of the endplates of the superior and inferior vertebral bodies V, respectively. As illustrated in FIGS. 10A-10C, the superior and inferior bone contacting components 22, 32 are better able to adapt and/or conform to the endplates of the superior and inferior vertebral bodies V, respectively, due to the inherent flexibility or adaptability of forming the superior and inferior bone contacting members 20, 30 from multiple components 22, 32 interconnected by a flexible wire netting 50, 50'. Thus, in use, the lateral wire netting 50' enables the superior bone contacting components 22 to move with respect to one another and enables the inferior bone contacting components 32 to move with respect to one another such that the lateral wire netting 50' enables the superior and inferior bone contacting members 20, 30 to adapt and/or conform to the endplates of the superior and inferior vertebral bodies V, respectively.

The preferred implant 10 also includes a cavity 40 located between the superior and inferior bone contacting members 20, 30. The cavity 40 is preferably sized and configured to receive a filling material (not shown) and/or a balloon 75, an expansion sack, an expansion bag, etc. (collectively referred to herein as an "expansion member"). The expansion member 75 is preferably sized and configured to be received within the cavity 40 in order to limit any filling material from overflowing and escaping from the cavity 40. More preferably, as will be described in greater detail below, once the implant 10 has been implanted and positioned, the expansion member 75 is preferably inserted into the cavity 40. Thereafter, the filling material may be inserted into the expansion member 75, expanding the expansion member 75 so that the implant 10 is expanded from the collapsed, non-expanded or first insertion configuration to the second expanded configuration. Once inserted, the filling material preferably hardens or is cross-linked in order to support the implant 10 in the second expanded configuration. Alternatively, the filling material may not harden and may partially harden into a gel-like material or may retain a flowable or liquid state and become sealed in the expansion member 75.

It should be noted that expanding of the expansion member 75 may or may not cause distraction of the adjacent vertebral bodies V. However, the flexibility of the expansion member 75 and the sequential hardening of the filling material preferably provide a geometrically adapted restoration of the intervertebral disc space S. Alternatively, the filling material may remain in a gel and/or liquid state and may be sealed in the expansion member 75. In addition, as will be generally appreciated by one of ordinary skill in the art, the expansion member 75 may be inserted into the cavity 40 prior to implantation of the implant 10, the filling material may be injected into the expansion member 75 prior to implantation of the implant 10, the expansion member 75 may be integrated with or coupled to the implant 10, and/or the expansion member 75 may be omitted entirely.

Moreover, it should be understood that the superior and inferior bone contacting members 20, 30 may include any number of bone contacting components 22, 32 and interconnecting lateral wire netting 50' such as, for example, three bone contacting components 22, 32 interconnected by two lateral wire nettings 50'. It is also envisioned that the implant 10 may include one or more intermediate components (not shown) between the superior and inferior bone contacting members 20, 30. The intermediate components may be coupled to the superior and inferior bone contacting members 20, 30 via the vertical wire netting 50. Moreover, it is also envisioned that the implant 10 may include the vertical wire netting 50 to enable cranio/caudal expansion without incorporating the lateral wire netting 50'. Alternatively, the implant 10 may include the lateral wire netting 50' to enable lateral expansion without incorporating the vertical wire netting 50.

The superior and inferior bone contacting members 20, 30 may include means for increasing the stability of the implant 10, such as, for example, one or more projections, one or more roughened surfaces, one or more undulating structures, one or more ridges, one or more keels, etc. Preferably, the superior and inferior bone contacting members 20, 30 include a plurality of teeth 21 for increasing the stability of the implant 10.

The implant 10 may also include a mechanism or feature for engaging an implant insertion instrument (not shown).

The mechanism or feature for engaging the insertion instrument may take on any form now or hereafter known including, for example, one or more bores 102 for receiving one or more projections (not shown) formed on the implant insertion instrument, one or more projections (not shown) for engaging one or more bores (not shown) formed on the implant insertion instrument, one or more channels (not shown) for receiving one or more tips formed on the implant insertion instrument, one or more threaded bores (not shown) for receiving one or more threaded shafts or screws, etc.

The implant 10 may also include a mechanism or features for reducing and/or preventing shearing or dismantling of the implant 10 during insertion such as, for example, the superior and inferior bone contacting members 20, 30 may include interconnecting projections 24 and bores 34 for temporarily securing the implant 10 in its collapsed or insertion configuration.

The superior and inferior bone contacting members 20, 30 may be formed from any biocompatible material including, but not limited to, a metal, such as, for example, cobalt-chromium-molybdenum (CCM) alloys, titanium, titanium alloys, stainless steel, aluminum, etc., a ceramic such as, for example, zirconium oxide, silicone nitride, etc., an allograft, an autograft, a metal-allograft composite, a polymer such as, for example, polyaryl ether ketone (PAEK), polyether ether ketone (PEEK), polyether ketone ketone (PEKK), polyetherketone (PEK), polyetherketone ether-ketone-ketone (PEK-EKK), etc. The polymers may be reinforced with a fiber such as, for example, a carbon fiber or other thin, stiff fiber.

The superior and inferior bone contacting members 20, 30 may also be coated in order to enhance their osteo-conductive properties. For example, the bone contacting members 20, 30 may be coated with an etching, anodization, an anodic plasma chemical process, electrolytic deposition, plasma spraying, a thin layer of titanium (Ti) via a physical or chemical vapor deposition process, an anodic plasma chemical surface treatment incorporating, for example, Ca and/or P in the Ti-Oxide surface layer or via a Ti or HA plasma spray, etc.

The expansion member 75 may be manufactured from any biocompatible material including, but not limited to, a polyurethane, a polycarbonate urethane, a poly carbonate-silicone urethane copolymer, polyamine, polyethylene terephthalate (PET), polycaprolactone, etc.

The filling material may be any biocompatible material known in the art and may be a rigid or elastic material. The filling material may be comprised of, for example, a bone cement, a hydrogel, a polyvinyl alcohol, a sodium polyacrylate, an acrylate polymer, a methyl-methacrylate, a co-polymer with an abundance of hydrophilic groups, p-vinyl pyrollidone, polyethyleneimine, etc., a setting or curing hydrogel based co-polymer such as, for example, polyethyleneimine, poly(diethylaminoethyl methacrylate), poly(ethylaminoethyl methacrylate), etc., a thermally setting hydrogel based co-polymers, such as, for example, poly-N-isopropylacrylamide with polyethylene glycol, copolymers of polyethylene oxide and polyphenelylene oxide, copolymers of polyethylene glycol and polyactides, etc., an ionic setting hydrogel such as, for example, ethylacrylate, methacrylic acid, 1,4-butanediacrylate, etc., or a PCU, PCU-silicone co-polymer, silicone or other non-resorbable pure or elastic co-polymer (e.g., PCU's silicone end group modified PU's, RTV curing siloxane based elastomers, etc.).

Exemplary Method of Inserting the Intervertebral Implant

The expandable intervertebral implant 10 may be inserted within the targeted intervertebral disc space S by any means, method, or approach now or hereafter known in the art including, but not limited to, via anterior, lateral, posterior, anterior-lateral, or posterior-lateral approaches, etc. Preferably, the implant 10 is implanted using a minimally invasive technique. Alternatively, the implant 10 may be implanted via an open incision, as would be appreciated by one having ordinary skill in the art.

Referring to FIGS. 11A-11E, in one exemplary method of inserting the implant 10 via a lateral approach, the implant 10 is inserted into the intervertebral disc space S between adjacent superior and inferior vertebral bodies V via an insertion instrument (not shown). As illustrated in FIG. 11A, the implant 10 is preferably inserted into the intervertebral disc space S in the collapsed, non-expanded or first insertion configuration following a preferably minimal incision through the skin to the disc space S. As illustrated in FIG. 11B, the implant 10 is preferably positioned within the intervertebral disc space S at least partially in a posterior direction in order to generally keep the motion segment in balance. More preferably, the implant 10 should be positioned so that the implant 10 engages the stronger peripheral aspects of the adjacent vertebral bodies V. Once the implant 10 has been properly positioned in its desired location, as illustrated in FIG. 11C, the implant 10 is preferably laterally expanded in the anterior-posterior direction (in the lateral direction if the implant 10 was inserted via an anterior or posterior approach) via a surgical instrument (not shown). Alternatively, the implant 10 may be inserted with the expansion member or balloon 75 therein and laterally expanded via the expansion member 75. Preferably, the implant's position should be checked at this point to ensure preferred positioning. Once the position of the implant 10 is verified based generally on surgeon preference and/or physiology, as illustrated in FIG. 11D, the expansion member 75 is inserted and positioned within the cavity 40 formed in the implant 10 via an insertion instrument (not shown). The implant 10 may be slightly expanded via the implant insertion instrument in order to ease insertion of the expansion member 75 within the cavity 40, if necessary. Next the expansion member 75 is filled with a filling material, which causes the implant 10 to expand in the cranio/caudal direction, preferably resulting in the implant 10 firmly penetrating into the endplates of the adjacent superior and inferior vertebral bodies V. Due to the adaptability of the vertical and/or lateral wire netting 50, 50', the superior and inferior bone contacting members 20, 30 of the implant 10 may substantially mate to the typically uneven surfaces of the endplates of the superior and inferior vertebral bodies V, respectively. For example, the individual bone contacting members 22, 32 may move linearly relative to each other along the longitudinal, lateral and/or vertical axes A1, A2, A3 and may pivot relative to each other about the longitudinal, lateral and/or vertical axes A1, A2, A3 such that the shape of the implant 10 in the expanded configuration conforms to the anatomical shape of the pre-existing endplates of the vertebrae V. Specifically, each of the bone contacting members 22, 32 are movable relative to each other in six degrees of freedom to permit the individual components to adapt their final position to the patient's anatomy, thereby reducing stress risers that may develop when an implant is unable to conform to the shape of the anatomy.

Exemplary Method of Manufacturing the Intervertebral Implant

The preferred expandable intervertebral implant 10 may be manufactured by any means and/or method now or hereafter known in the art including, but not limited to, by manufacturing each of the bone contacting members 20, 30 as separate and distinct components and then coupling each of the components to vertical and lateral wire netting 50, 50', as required.

Preferably, however, the implant 10 is formed as an integral implant manufactured via a layer-wise or layer by layer manufacturing process. For example, referring to FIGS. 12A-12L, the implant 10 preferably is manufactured via a selective laser melting process. The metal components are preferably set up in layers, similar to a stereo-lithograph. In use, a thin layer of metal powder is applied to a platform. The powder is then locally melted by, for example, a laser beam. The platform is then lowered by a defined layer height. Another thin layer of metal powder is then applied. The second layer of powder is then locally melted. This process is repeated until the implant 10 is complete. The ability to manufacture the implant 10 as a single or integral component or part permits the manufacture of continuous loops or solid vertical and lateral wire netting 50, 50' between the bone contacting components 22, 32. In contrast, alternate techniques for constructing the vertical and lateral wire netting 50, 50' may require joining together of ends of the wires to construct the preferred first, second, third and fourth link members 52, 52', 52", 52'".

Alternatively, the implant 10 may be manufactured via a selective laser sintering process. Generally, the laser sintering process follows the same steps as the selective laser melting process described above. However since sintering is performed below the melting point of the substrate material, the laser sintering process allows the original metal powder to be mixed with a binding agent. A steam stripping process may be used after the laser sintering process. Using the laser sintering process, combinations of metals as well as microporous structures can be manufactured. The laser sintering process may also be used in connection with thermoplastic polymers which do not have any specific melting point but rather have a transition zone between a glass transition temperature and a melt mass temperature.

While laser melting and sintering processes have been described, other manufacturing methods are contemplated including, but not limited to, other methods of curing or sintering such as, for example, the use of ultrasonic or ultraviolet rays.

Features described herein may be used singularly or in combination with other features. In addition, features disclosed in connection with one embodiment may be interchangeable with a feature or features disclosed in another embodiment. Therefore the presently disclosed embodiments are to be considered as illustrative and not restrictive, the scope of the invention being indicated by the appended claims, and not limited to the foregoing description.

It will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the appended claims.

What is claimed:

1. An expandable intervertebral implant configured to be implanted in an intervertebral space between adjacent superior and inferior vertebral bodies, the implant comprising:
    a first outer member having a first outer surface configured to face one of the superior and inferior vertebral bodies when the implant is disposed in the intervertebral space, and a first inner surface opposite the first outer surface along a first direction, the first outer member defining a plurality of openings that extend into the first inner surface towards the first outer surface; and
    a second outer member having a second outer surface configured to face another one of the superior and inferior vertebral bodies when the implant is disposed in the intervertebral space, a second inner surface opposite the second outer surface along the first direction, and a plurality of protrusions, each protrusion extending from the second inner surface to a terminal end of the protrusion in a direction that is away from the second outer surface, wherein the first and second outer surfaces are opposite each other along the first direction,
    wherein the implant is configured to expand from a collapsed configuration to an expanded configuration in response to expansion of a balloon that is disposed in an internal space of the implant, thereby increasing a height of the implant that is defined from the first outer surface to the second outer surface, such that the first and second outer surfaces bear against respective ones of the superior and inferior vertebral bodies, and
    wherein the plurality of protrusions are disposed in the plurality of openings when the implant is in the collapsed configuration and are removed from the plurality of openings when the implant is in the expanded configuration such that the terminal ends of the protrusions are exposed within the internal space of the implant.

2. The expandable intervertebral implant of claim 1, wherein the implant has a first end and a second end that are spaced from one another along a longitudinal direction, perpendicular to the first direction, and first and second sides that are spaced from one another along a lateral direction, perpendicular to the both the first direction and the longitudinal direction.

3. The expandable intervertebral implant of claim 2, wherein some of the plurality of protrusions are spaced from one another along the longitudinal direction.

4. The expandable intervertebral implant of claim 3, wherein some of the plurality of protrusions are spaced from one another along the lateral direction.

5. The expandable intervertebral implant of claim 2, wherein the plurality of protrusions comprises first to fourth protrusions, wherein the first and second protrusions are offset from the third and fourth protrusions with respect to the longitudinal direction.

6. The expandable intervertebral implant of claim 5, wherein the first and third protrusions are offset from the second and fourth protrusions with respect to the lateral direction.

7. The expandable intervertebral implant of claim 2, wherein the implant is elongate along the longitudinal direction from the first end to the second end.

8. The expandable intervertebral implant as recited in claim 1, wherein each of the plurality of openings extends into the first inner surface towards the first outer surface along the first direction.

9. The expandable intervertebral implant as recited in claim 8, wherein each of the openings has a fully enclosed outer perimeter in a plane that is oriented perpendicular to the first direction.

10. The expandable intervertebral implant as recited in claim 9, wherein the fully enclosed outer perimeter defines a round surface in the plane.

11. The expandable intervertebral implant as recited in claim 10, wherein the round surface follows a circular path.

12. A system, comprising:
the expandable intervertebral implant of claim 1; and
the balloon, wherein the balloon is configured to bear against each of the first and second outer members as it expands.

13. An expandable intervertebral implant configured to be implanted in an intervertebral space between adjacent superior and inferior vertebral bodies, the implant comprising:
a first outer member having a first outer surface configured to face one of the superior and inferior vertebral bodies, and a first inner surface opposite the first outer surface, the first outer member defining a plurality of recesses that extend therein; and
a second outer member having a second outer surface configured to face another one of the superior and inferior vertebral bodies, a second inner surface opposite the second outer surface, first and second arms that extend from the second inner surface along a select direction, and a plurality of protrusions that extend from the first and second arms along the select direction such that each protrusion is configured to be at least partially inserted into a complementary one of the plurality of recesses,
wherein the implant is configured to expand from a collapsed configuration to an expanded configuration in response to expansion of a balloon that is disposed in an internal space of the implant, thereby increasing a height of the implant that is defined from the first outer surface to the second outer surface, such that the first and second outer surfaces bear against respective ones of the superior and inferior vertebral bodies.

14. The expandable intervertebral implant of claim 13, wherein the implant has a select configuration wherein a portion less than an entirety of each of the plurality of protrusions is received in the complementary one of the plurality of recesses.

15. The expandable intervertebral implant of claim 14, wherein the select configuration is between the collapsed configuration and the expanded configuration.

16. The expandable intervertebral implant of claim 13, wherein the implant has a first end and a second end that are spaced from one another along a longitudinal direction, and the implant is elongate along the longitudinal direction.

17. The expandable intervertebral implant of claim 16, wherein some of the plurality of protrusions are spaced from one another along the longitudinal direction.

18. The expandable intervertebral implant of claim 17, wherein the first and second outer surfaces are opposite each other along a first direction, and some of the plurality of protrusions are spaced from one another along a lateral direction that is perpendicular to each of the longitudinal direction and the first direction.

19. The expandable intervertebral implant of claim 13, wherein the plurality of protrusions comprises a first and second pairs of protrusions that are spaced from one another along the lateral direction, and the internal space is defined between the first and second pairs of protrusions with respect to the lateral direction.

20. A system, comprising:
the expandable intervertebral implant of claim 13; and
the balloon.

21. The expandable intervertebral implant of claim 1, wherein the first and second outer members are coupled to one another when the implant is in the collapsed and expanded configurations.

* * * * *